United States Patent
Ahmad et al.

(10) Patent No.: US 11,672,758 B2
(45) Date of Patent: *Jun. 13, 2023

(54) ENDOXIFEN METHODS AND COMPOSITIONS FOR INHIBITION OF PROTEIN KINASE C

(71) Applicant: Jina Pharmaceuticals, Inc., Libertyville, IL (US)

(72) Inventors: Ateeq Ahmad, Wadsworth, IL (US); Shoukath M. Ali, Vernon Hills, IL (US); Moghis U. Ahmad, Wadsworth, IL (US); Saifuddin Sheikh, Waukegan, IL (US); Imran Ahmad, Libertyville, IL (US)

(73) Assignee: JINA PHARMACEUTICALS, INC., Libertyville, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/023,208

(22) Filed: Sep. 16, 2020

(65) Prior Publication Data

US 2021/0177752 A1    Jun. 17, 2021

Related U.S. Application Data

(63) Continuation of application No. 16/376,053, filed on Apr. 5, 2019, now abandoned, which is a continuation (Continued)

(51) Int. Cl.
*A61K 9/20* (2006.01)
*A61K 31/138* (2006.01)
(Continued)

(52) U.S. Cl.
CPC .......... *A61K 9/06* (2013.01); *A61K 9/08* (2013.01); *A61K 9/19* (2013.01); *A61K 31/138* (2013.01); *A61K 9/0014* (2013.01); *Y02A 50/30* (2018.01)

(58) Field of Classification Search
None
See application file for complete search history.

(56) References Cited

U.S. PATENT DOCUMENTS

| 4,310,523 A | 1/1982 | Neumann |
|---|---|---|
| 6,090,407 A | 7/2000 | Knight et al. |
| (Continued) | | |

FOREIGN PATENT DOCUMENTS

| WO | WO 2008/058156 | 5/2008 |
|---|---|---|
| WO | WO 2008/070463 | 6/2008 |
| WO | WO 2008/127358 | 10/2008 |

OTHER PUBLICATIONS

Johnson et al. Pharmacological characterization of 4-hydroxy-N-desmethyl tamoxifen, a novel active metabolite of tamoxifen, Breast Cancer Researc=h and treatment 85:151-159 (Year: 2004).*

(Continued)

*Primary Examiner* — Lakshmi S Channavajjala
(74) *Attorney, Agent, or Firm* — Casimir Jones, S.C.; Mary Ann D. Brow

(57) ABSTRACT

The present invention provides compositions containing endoxifen, formulations and liposomes of endoxifen, methods of preparation of such agents and formulations, and use of such agents and formulations for the treatment of a subject having or at risk for psychiatric and neurodegenerative diseases. Specifically, the present invention relates to the composition comprising endoxifen in the treatment of bipolar disorder, schizophrenia, multiple sclerosis (MS), Alzheimer disease, Parkinson disease, Huntington's disease, amyotrophic lateral sclerosis (ALS), and/or epilepsy by administrating formulations or compositions comprising an effective amount of endoxifen.

3 Claims, 5 Drawing Sheets

Related U.S. Application Data of application No. 12/470,219, filed on May 21, 2009, now abandoned, which is a continuation-in-part of application No. 12/515,261, filed as application No. PCT/US2007/085443 on Nov. 21, 2007, now Pat. No. 9,333,190.

(60) Provisional application No. 60/860,420, filed on Nov. 21, 2006, provisional application No. 60/860,788, filed on Nov. 22, 2006.

(51) Int. Cl.
*A61K 9/06* (2006.01)
*A61K 9/08* (2006.01)
*A61K 9/19* (2006.01)
*A61K 9/00* (2006.01)

(56) References Cited

U.S. PATENT DOCUMENTS

| | | | |
|---|---|---|---|
| 6,290,991 | B1 | 9/2001 | Roser et al. |
| 6,638,767 | B2 | 10/2003 | Unger et al. |
| 9,333,190 | B2 | 5/2016 | Ahmad et al. |
| 10,376,479 | B2 * | 8/2019 | Ahmad ............... A61K 9/48 |
| 2005/0038111 | A1 * | 2/2005 | Bateman ............ A61K 31/56 |
| | | | 514/522 |
| 2005/0158388 | A1 | 7/2005 | Le Nestour et al. |
| 2009/0291134 | A1 | 11/2009 | Ahmad et al. |
| 2012/0164075 | A1 | 6/2012 | Ahmad et al. |
| 2016/0346230 | A1 | 12/2016 | Ahmad et al. |

OTHER PUBLICATIONS

Adedoyin et al., Pharmacokinetic profile of ABELCET (amphotericin B lipid complex injection): combined experience from phase I and phase II studies. Antimicrob Agents Chemother. Oct. 1997;41(10):2201-8.
Alkon et al., PKC signaling deficits: a mechanistic hypothesis for the origins of Alzheimer's disease. Trends Pharmacol Sci. Feb. 2007;28(2):51-60.
Assersohn et al., Studies of the potential utility of Ki-67 as a predictive molecular marker of clinical response in primary breast cancer. Breast Cancer Res Treat. 2003;82:113-123.
Bhatia, Tamoxifen in topical liposomes: development, characterization and in-vitro evaluation. J Pharm Pharm Sci. Jul. 16, 2004;7(2):252-9.
Borges et al., Quantitative effect of CYP2D6 genotype and inhibitors on tamoxifen metabolism: implication for optimization of breast cancer treatment. Clin Pharmacol Ther. Jul. 2006;80(1):61-74.
Einat et al., Protein kinase C inhibition by tamoxifen antagonizes manic-like behavior in rats: implications for the development of novel therapeutics for bipolar disorder. Neuropsychobiology. 2007;55(3-4):123-31.
Etcheberrigaray et al., Therapeutic effects of PKC activators in Alzheimer's disease transgenic mice. Proc Natl Acad Sci U S A. Jul. 27, 2004;101(30):11141-6.
Fisher et al., Tamoxifen for prevention of breast cancer: Report of the National Surgical Adjuvant and Bowel Project P-1 Study. J. Natl Cancer Insts 1998; 90:1371-88.
Furr, et al. The pharmacology and clinical uses of Tamoxifen. Pharmacol Ther 1984; 25:127-205.
Gad, Active drug metabolites in drug development. Curr Opin Pharmacol. Feb. 2003;3(1):98-100.
Goetz et al. Pharmacogenetics of Tamoxifen Biotransformation Is Associated With Clinical Outcomes of Efficacy and Hot Flashes. JCO Dec. 20, 2005: 9312-9318.
Hann et al., Lipid-based amphotericin B: a review of the last 10 years of use. Int J Antimicrob Agents. Mar. 2001;17(3):161-9.
Hongpaisan et al., PKC $\epsilon$ activation prevents synaptic loss, A$\beta$ elevation, and cognitive deficits in Alzheimer's disease transgenic mice. J Neurosci. Jan. 12, 2011;31(2):630-43.
Johnson, et al. Pharmacological characterization of 4-hydroxy-N-desmethyl tamoxifen, a novel active metabolite of Tamoxifen. Breast Cancer Res Treat. 2004;85(2):151-159.
Johnston et al., Iodoxifen Antagonizes Estradiol-dependent MCF-7 Breast Cancer Xenograft Growth through Sustained Induction of Apoptosis. Cancer Research. 1999;59:3646-3651.
Kenny et al., Change in expression of ER, bcl-2 and MIB-1 on primary Tamoxifen and relation to response in ER positive breast cancer. Breast Cancer Res Treat. 2001;65:135-144.
Lee et al., Quantification of tamoxifen and three metabolites in plasma by high-performance liquid chromatography with fluorescence detection: application to a clinical trial. J Chromatogr B Analyt Technol Biomed Life Sci. 2003;791(1-2):245-253.
Lim et al. Endoxifen (4-hydroxy-N-desmethyl-Tamoxifen) has anti-estrogenic effects in breast cancer cells with potency similar to 4-hydroxy-Tamoxifen. Journal of Cancer Chemotherapy and Pharmacology 2005:55:471-478.
Lim et al. Endoxifen has antiestrogenic effects in breast cancer cells with potency similar to 4-hydroxy-tamoxifen. Proceedings of American Cancer Research, vol. 45, 2004 abstract #3758, 1 pg.
Lim et al., Endoxifen, a Secondary Metabolite of Tamoxifen, and 4-OH-Tamoxifen Induce Similar Changes in Global Gene Expression Patterns in MCF-7 Breast Cancer Cells. J Pharm and Exp Thera. 2006;318:503-512.
Lino et al., Reversible Control of Oestradiol-stimulated Growth of MCF-7 Tumours in the Athymic Mouse. Br. J. Cancer. 1991;64:1019-1024.
Malet et al., Effect of 4-hydroxytamoxifen isomers on growth and ultrastructural aspects of normal human breast epithelial (HBE) cells in culture. J Steroid Biochem Mol Biol. Nov. 2002;82(4-5):289-96.
Manji et al., Bipolar disorder: leads from the molecular and cellular mechanisms of action of mood stabilisers. Br J Psychiatry. Jun. 2001;178(Suppl 41):S107-19.
Mauvais-Jarvis et al., trans-4-Hydroxytamoxifen concentration and metabolism after local percutaneous administration to human breast. Cancer Res. Mar. 1986;46(3):1521-5.
Merriam-Webster, Definition of "Complex", https://merriam-webster.com/dictionary/complex, retrieved Aug. 20, 2018,1 page.
Merriam-Webster, Definition of "Synthetic", https://merriam-webster.com/dictionary/synthetic, retrieved Aug. 20, 2018, 1 page.
Nahta et al., Growth factor Receptors in Breast Cancer: Potential for Therapeutic Intervention. Oncologist. 2003;8:5-17.
Osborne, Tamoxifen in the treatment of breast cancer. N Engl J Med 1998;339:1609-18.
Otton et al., Venlafaxine oxidation in vitro is catalyzed by CYP2D6. Br J Clin Pharmacol 1996; 41:149-56.
Pujol et al., Phase 1 study of percutaneous 4-hydroxy-tamoxifen with analyses of 4-hydroxy-tamoxifen concentrations in breast cancer and normal breast tissue. Cancer Chemother Pharmacol. 1995;36(6):493-8.
Reddy et al., Tamoxifen citrate loaded solid lipid nanoparticles (SLN): preparation, characterization, in vitro drug release, and pharmacokinetic evaluation. Pharm Dev Technol. 2006;11(2):167-77.
Saltstein et al., Prevention and Management of Biclutamide-induced gynecomastia and Breast Pain: Randomized Endocrinologic and Clinical Studies with Tamoxifen and Anastrozole. Prostate Cancer and Prostatic Diseases 2005;8:75-83.
Sarkaria et al., Tamoxifen-induced increase in the Doubling time of MCF-7 Xenografts as Determined by Bromodeoxyuridine Labeling and Flow Cytometry. Cancer Research 1993;53:4413-4417.
Satyavati, Guggulipid: a Promising Hypolipidaemic Agent from Gum Guggul (*Commiphora wightii*). Economic and Medical Plant Research. 1991;5:47-82.
Stearns et al., Active Tamoxifen metabolite concentrations after co-administration of Tamoxifen and the selective serotonin reuptake inhibitor paroxetine. J Natl Cancer Inst 2003;95:1758-1764.
Stearns et al., Hot flushes. Lancet 2002; 360:1851-61.

(56) References Cited

OTHER PUBLICATIONS

Suh et al., Arzoxifene, a New Selective Estrogen receptor Modulator For Chemo prevention of Experimental Breast Cancer. Cancer Research. 2001;61:8412-8415.
Zeisiq et al., Reduction of tamoxifen resistance in human breast carcinomas by tamoxifen-containing liposomes in vivo. Anticancer Drugs. Aug. 2004;15(7):707-14.
U.S. Appl. No. 60/860,420, filed Nov. 21, 2006, 36 pages.
U.S. Appl. No. 60/860,788, filed Nov. 22, 2006, 36 pages.
Communication of a Notice of Opposition for EP Pat. 2101731, dated Nov. 12, 2018, 34 pages.
Communication of a Notice of Opposition for EP Pat. 2101731, dated Nov. 7, 2018, 30 pages.

* cited by examiner

ENDOXIFEN METHODS AND COMPOSITIONS FOR INHIBITION OF PROTEIN KINASE C

This application is a Continuation of U.S. application Ser. No. 16/376,053, filed Apr. 5, 2019, which is a Continuation of U.S. application Ser. No. 12/470,219, filed May 21, 2009, now abandoned, which is a Continuation-in-Part of U.S. application Ser. No. 12/515,261, filed May 15, 2009, now U.S. Pat. No. 9,333,190, which is a 371 National Stage Application of International Application No. PCT/US07/85443, filed Nov. 21, 2007, which claims priority to U.S. Provisional Application Ser. No. 60/860,420, filed Nov. 21, 2006, and 60/860,788, filed Nov. 22, 2006, each of which is incorporated herein by reference.

FIELD OF THE INVENTION

The invention relates to the use of endoxifen in the treatment of mammalian diseases. The invention also relates to liposomes and other formulations such as complexes, vesicles, emulsions, micelles and mixed micelles of endoxifen, methods of preparation, and uses, e.g., in the treatment of human and animal breast diseases. The invention in particular relates to compositions comprising endoxifen-lipid complexes, methods of preparation, and their use for the treatment of breast diseases, in particular benign and malignant breast disease, enhancing disease regression and reducing risk of patients developing breast cancer. This invention further relates to the endoxifen and compositions comprising endoxifen in the treatment of psychiatric and neurodegenerative diseases. In particular, the present invention further relates to the use of compositions comprising endoxifen in the treatment of bipolar disease, schizophrenia, multiple sclerosis (MS), Alzheimer disease, Parkinson disease, Huntington's disease, amyotrophic lateral sclerosis (ALS), and epilepsy The invention still further relates to methods of preparing endoxifen and use of endoxifen prepared by inventive method in the treatment of human and animal diseases.

BACKGROUND OF THE INVENTION

Every year more than 210, 000 women in the United States develop breast cancer. One in eight women in the US will develop breast cancer during their lives. Approximately 70 percent of breast cancers are fueled by estrogen, and many are treated with tamoxifen, a drug designed to block the effects of estrogen in breast tissue.

Tamoxifen is an anti-estrogenic drug prescribed for long-term, low dose therapy of breast cancer. It has been widely used for more than 30 years for the endocrine treatment of all stages of hormone receptor-positive breast cancer (1, 2). Tamoxifen has also been approved for the prevention of breast cancer (3). In women, one of the adverse events associated with tamoxifen is hot flashes. The risk of hot flashes is two to three-folds higher among women who take tamoxifen than it is for those who do not (4, 5). Selective serotonin-reuptake inhibitor (SSRI) antidepressants are prescribed to treat hot flashes. However, some SSRIs, such as paroxetine and fluoxetine, are known to inhibit cytochrome P450 (CYP) 2D6 (6), an enzyme that is important for the metabolism of many drugs, including tamoxifen (5). Furthermore, there is a large inter-individual and ethnic variability in tamoxifen metabolism due to CYP2D6 genetic polymorphism affecting its expression and function (7). Thus, the understanding of tamoxifen metabolism and effect has changed clinical practice through the wide spread recognition that the co-prescription of drugs that inhibit CYP2D6 may compromise tamoxifen efficacy.

Bipolar disorder is a chronic mental illness that is associated with a substantial risk of suicide among those affected (8). Lithium and valproate are widely used as mood stabilizers in bipolar disorder, however, a substantial minority of patients fails to respond, or respond only partially, to these agents (8). Therefore, the development of novel therapeutic agents with a quicker, more potent, and more specific mode(s) of action with fewer side effects are required.

Tamoxifen is a selective estrogen receptor modulator (SERM). Recent investigations strongly support a therapeutic role of estrogen/SERMs in psychiatric diseases (e.g., bipolar disorder, schizophrenia) and a neuroprotective effect in neurodegenerative conditions (e.g., multiple sclerosis, Parkinson disease, Alzheimer disease, and stroke). In a rat model of mania (9) and in two clinical trials with bipolar patients (10, 11). This is suggested to be attributed to attenuation of the actions of protein kinase C (PKC) (WO 2008/048194 to Yesilogluj). Tamoxifen use also showed improvement in manic symptoms in patients with schizoaffective disorder (12), and several neuroprotective effects of tamoxifen have been documented (13, 14). Furthermore, there is evidence that tamoxifen may have neurotrophic effects, e.g., by increasing synaptic density and stimulating neurite outgrowth (13). However, as noted in the discussion, above, the efficacy of treatment using tamoxifen can be compromised by other drugs or by mutations that disrupt the metabolism of the drug.

A strong need exists for methods of using SERMs in therapy, with reduced adverse systemic side effects. In addition, there is a need for methods and compositions to treat and prevent diseases such as breast cancer and bipolar disorder with compositions having reduced interactive effect with other medications, and reduced sensitivity to patient genetics involving mutations in genes encoding key drug metabolizing enzymes.

SUMMARY OF THE INVENTION

The present invention provides methods and compositions for the syntheses and use of active agents such as anticancer agents and agents for treatment of psychiatric and neurodegenerative conditions. The present invention relates to methods and compositions related to the formulations and uses of endoxifen, particularly in applications related to the treatment or prevention of cancer, and in the treatment and prevention of psychiatric and neurodegenerative disease.

The compositions of the present invention can be employed to treat psychiatric and neurodegenerative diseases. For example, the compositions of the present invention may be administered to a patient diagnosed with bipolar disorder or manic disorder. The exemplary examples of psychiatric and neurodegenerative diseases treatable by the present inventive compositions include but not limited to bipolar disorder, Alzheimer's disease, Parkinson's disease, multiple sclerosis diseases, epilepsy, and the like.

ENDOXIFEN (4-hydroxy N-desmethyl tamoxifen) is an active metabolite of the marketed drug tamoxifen for the treatment of breast cancer. Tamoxifen is extensively metabolized by cytochrome P450 (CYP) enzymes CYP3A4 and CYP2D6 into active metabolites including 4-hydroxy tamoxifen and 4-hydroxy-N-desmethyl tamoxifen (endoxifen) (FIG. 3). The use of endoxifen as a therapeutic agent e.g., for cancer, and psychiatric and neurodegenerative diseases has significant advantages compared to use of the mother compound tamoxifen, which requires metabolic activation by cytochrome P450 (CYP) enzymes whose actions are variable because of genetic polymorphism and inhibition via drug-drug interaction.

In some embodiments, the present invention provides a method of treating a disease, comprising, preparing a composition comprising a therapeutically active amount of endoxifen and administering the composition. In some embodiments, the endoxifen is a free base, or is in the form of a salt. In some preferred embodiments, the endoxifen is in the form of a salt selected from the group of salts consisting of citrate, acetate, formate, sulfonate, oxalate, succinate, tartarate, trifluoroacetate, methane sulfonate, phosphate, sulfate, chloride, bromide, iodide, and lactate. In preferred embodiments, the salt is in the form of citrate. In some embodiments, the endoxifen is predominantly in a form selected from the group consisting of E-isomer, Z-isomer, and a mixture of E- and Z-isomer.

In some embodiments, method comprises preparing a complex comprising an anticancer or an psychiatric therapeutic drug and at least one lipid. In some embodiments, the drug is endoxifen. In some embodiments, the compounds of the invention are not complexed with a lipid. In some embodiments, the compound is in the form of a free base or is in the form of a salt.

In some embodiments, the present invention provides methods of preparing endoxifen, comprising reacting a compound of Formula 5 with acid, wherein the compound of formula 5 has the structure:

5

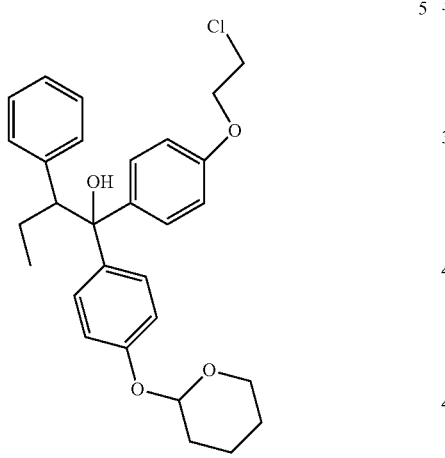

and, after the reaction of the compound of Formula 5 with acid, reacting the compound with methylamine. In some embodiments, the compound of Formula 5 is prepared by reacting compound of formula 4

4

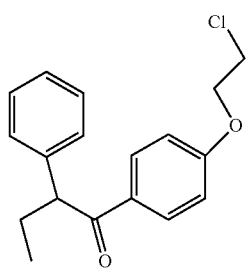

with a compound of Formula 3.

3

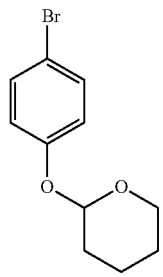

In some embodiments, the compound of Formula 3 is prepared by reacting compound of Formula 1

1

Br with a compound of Formula 2.

2

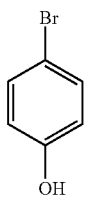

In some embodiments, the present invention provides methods of purifying the endoxifen as described above, comprising crystallizing the endoxifen and/or chromatographically treating said endoxifen to produce a purified preparation of endoxifen, wherein the purified preparation of endoxifen contains predominantly E-isomer, predominantly Z-isomer, or mixture of E- and Z-isomers of endoxifen.

As described above, in some embodiments, the invention provides endoxifen preparations comprising at least one lipid. In preferred embodiments, the at least one lipid is selected from the group consisting of egg phosphatidylcholine (EPC), egg phosphatidylglycerol (EPG), soy phosphatidylcholine (SPC), hydrogenated soy phosphatidylcholine (HSPC), dimyristoylphosphatidylcholine (DMPC), dimyristoylphosphatidylglycerol (DMPG), dipalmitoylphosohatidylcholine (DPPC), disteroylphosphatidylglycerol (DSPG), dipalmitoylphosphatidylglycerol (DMPG), cholesterol (Chol), cholesterol sulfate and its salts (CS), cholesterol hemisuccinate and its salts (Chems), cholesterol phosphate and its salts (CP), cholesterylphosphocholine and other hydroxycholesterol or amino cholesterol derivatives, cholesteryl succinate, cholesteryl oleate, polyethylene glycol derivatives of cholesterol (cholesterol-PEG), coprostanol, cholestanol, cholestane, cholic acid, cortisol, corticosterone, hydrocortisone, and calciferol, E-guggulsterone, Z-guggulsterone, mixture of E- and Z-guggulsterone, monoglycerides, diglycerides, triglycerides, carbohydrate-based lipids selected from a group consisting of galactolipid, mannolipid, galactolecithin, β-sitosterol, stigmasterol, stigmastanol, lanosterol, α-spinasterol, lathosterol, campesterol, phosphatidylcholine, phosphatidylglycerol, phosphatidylethanolamine, phosphatidylserine, phosphatdylinositol, phosphatidic acid, and pegylated derivatives of distearoylphosphatidylglycerol, dipalmitoylphosphatidylglycerol, dimyristoylphosphatidylglycerol, and dioleoylphosphatidylglycerol.

In some embodiments, a composition according to the present invention comprises endoxifen, cholesterol and/or cholesterol derivatives, and one or more phospholipids. In some preferred embodiments, the composition comprises a cholesterol derivative, and the cholesterol derivative is cholesteryl sulfate. In some embodiments, at least one of the phospholipids is hydrogenated soy phosphatidylcholine or soy phosphatidylcholine.

In some embodiments of the methods and compositions of the present invention, the composition comprises a form selected from the group consisting of powder, solution, emulsion, micelle, liposome, lipidic particle, gel, and paste form. In some preferred embodiments, the preparing of the composition comprising a complex comprises preparing said complex in a lyophilized form. In some embodiments, the preparing the complex in a lyophilized form comprises using a cryoprotectant, wherein said cryoprotectant comprises one or more sugars selected from the group consisting of trehalose, maltose, lactose, sucrose, glucose, and dextran. In some embodiments, the composition comprises a tablet or a filled capsule, wherein said tablet or filled capsule optionally comprises an enteric coating material.

In some embodiments of the treatment methods of the present invention, the disease is caused by cancer or by cancer-causing agents, while in some embodiments, the disease is benign breast disease.

In some embodiments, the administering comprises oral, intravenous, subcutaneous, percutaneous, parenteral, intraperitoneal, rectal, vaginal, and/or topical delivery said composition to said subject.

In some embodiments, the composition comprises a penetration enhancer, wherein said penetration enhancer comprises at least one saturated or unsaturated fatty acid ester.

In some embodiments, the composition comprising endoxifen is formulated in a hydroalcoholic gel, a hydroalcoholic solution, a patch, a cream, an emulsion, a lotion, an ointment, a powder or an oil.

In some embodiments, the composition comprising endoxifen is formulated in a hydroalcoholic composition containing a penetration enhancer, an aqueous vehicle, an alcoholic vehicle and a gelling agent.

In some embodiments, the hydroalcoholic composition comprises a neutralizing agent.

In some embodiments, the hydroalcoholic composition comprises endoxifen at about 0.01% to 0.20% by weight; isopropyl myristate at about 0.1% to 2.0%, preferably 0.5% to 2.0% by weight; alcohol at about 50.0% to 80.0%, preferably about 60.0% to 75.0% by weight; aqueous vehicle at about 20.0% to 60.0%, preferably 25.0% to 50.0% by weight; and gelling agent at about 1.0% to 10.0%, preferably about 0.5% to 5.0% by weight. In some embodiments, the wherein the percentage of components is weight to weight of the composition.

In some embodiments, the alcohol is ethanol or isopropanol, and constitutes in absolute form.

In some embodiments, the aqueous vehicle is a phosphate buffered solution.

In some embodiments, the gelling agent is selected from the group consisting of polyacrylic acid, hydroxypropylcellulose and a cellulose derivative other than hydroxypropylcellulose.

In some embodiments, the hydroalcoholic composition further comprises a neutralizing agent, wherein said neutralizing agent is selected from the group consisting of sodium hydroxide, potassium hydroxide, ammonium hydroxide, aminomethylpropanol, arginine, trolamine, and tromethamine, and wherein said neutralizing agent exists at a neutralizing agent/gelling agent ratio of about 1:1 to about 4:1.

In some embodiments, the invention provides methods of delivering endoxifen, comprising: providing any of the above described compositions and delivering the composition so as to expose the composition to a cell.

In some embodiments, the cell is in vivo.

In some embodiments of the invention, the host is a mammal.

The present invention also provides methods of inhibiting hormone-dependent breast carcinoma in a mammal comprising administering any of the above compositions to the mammal.

The present invention further provides methods of inhibiting a cancer in a mammal, said cancer including, but not limited to, lung cancer, colon cancer, breast cancer, leukemia, renal cancer, melanoma, cancer or the central nervous system, and prostate cancer in a mammal; the method comprising administering any of the above compositions to said mammal (e.g., a human).

The present invention further provides compositions comprising a therapeutically active amount of a complex comprising endoxifen and at least one lipid, wherein said endoxifen is a free base or is in the form of a salt.

In some embodiments, the composition comprising endoxifen is formulated in a hydroalcoholic gel, a hydroalcoholic solution, a patch, a cream, an emulsion, a lotion, an ointment, a powder or an oil.

In some embodiments, the composition comprising endoxifen is formulated in a hydroalcoholic composition containing a penetration enhancer, an aqueous vehicle, an alcoholic vehicle and a gelling agent.

In some embodiments, the hydroalcoholic composition comprises a neutralizing agent.

In some embodiments, the hydroalcoholic composition comprises endoxifen at about 0.01% to 0.20% by weight; isopropyl myristate at about 0.1% to 2.0%, preferably 0.5% to 2.0% by weight; alcohol at about 50.0% to 80.0%, preferably about 60.0% to 75.0% by weight; aqueous vehicle at about 20.0% to 60.0%, preferably 25.0% to 50.0% by weight; and gelling agent at about 1.0% to 10.0%, preferably about 0.5% to 5.0% by weight. In some embodiments, the wherein the percentage of components is weight to weight of the composition.

In some embodiments, the present invention provides methods of treating or preventing a condition in a subject (e.g., cancer, or a psychiatric or neurodegenerative condition) comprising administering a pharmaceutical preparation comprising a therapeutically effective amount of endoxifen.

Use of endoxifen compositions for psychiatric and neurodegenerative therapy is not limited to a particular disease or route of administration. In some preferred embodiments, the invention provides methods and compositions for treating bipolar disorder, while in other embodiments, the invention provides methods and compositions for treating multiple sclerosis, schizophrenia, Alzheimers' disease, Parkinson's disease, Huntington's disease, amyotrophic lateral sclerosis, and epilepsy.

In some embodiments, a pharmaceutical preparation of the present invention further comprises a second therapeutic agent. In some preferred embodiments, the second therapeutic is a known therapeutic agent for treatment of the condition. For example, in some embodiments, the second therapeutic agent is a known therapeutic for the treatment of bipolar disorder, manic disorder, or depression, e.g., lithium, a selective serotonin reuptake inhibitor, a serotonin and norepinephrine reuptake inhibitor, a dopamine reuptake inhibitor, a tetracyclic antidepressant, a combined reuptake inhibitor, a receptor blocker, tricyclic antidepressant, and a monoamine oxidase inhibitor. In some embodiments, the known therapeutic for the treatment of a psychiatric or neurodegenerative condition is selected from the group consisting of citalopram, escitalopram, fluoxetine, paroxetine, sertraline, duloxetine, venlafaxine, bupropion, mirtazapine, trazodone, tefazodone, maprotiline, amitriptyline, amoxapine, desipramine, doxepin, imipramine, nortriptyline, protriptyline, trimipramine, phenelzine, tranylcypromine, isocarboxazid, and selegilin.

In some embodiments in which a second therapeutic is co-administered with a composition comprising endoxifen, the second therapeutic is a known therapeutic agent for treatment of anxiety, such as a benzodiazepine, a beta-blocker, and a non-benzodiazepine hypnotic. In some preferred embodiments, the therapeutic for the treatment of anxiety is selected from the group consisting of diazepam, nitrazepam, alprazolam, bromazepam, chlordiazepoxide, chlorazepate, lorazepam, oxazepam, flunitrazepam, flurazepam, loprazolam, lormetazepam, and temazepam, buspirone, meprobamate, zalepon, zolpidem, zopiclone, chloral hydrate, triclofos, clomethizole, and meprobamate.

Particular embodiments of the invention are described in this Summary, and below, in the Detailed Descriptions of the Invention. The present invention is not limited to the compositions and methods described above. Although the invention has been described in connection with specific embodiments, it should be understood that the invention as claimed should not be unduly limited to such specific embodiments, and that variations of the compositions and methods described herein, or that are understood by a skilled artisan in view of the present disclosure, are included within the invention.

DEFINITIONS

Figure 1:
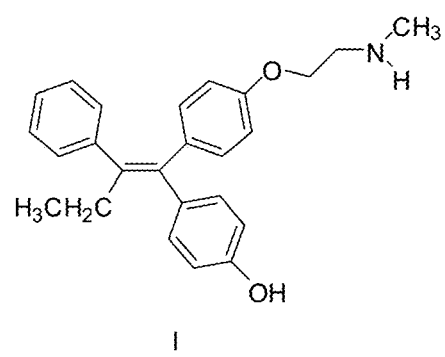
FIG. 1 diagrams compound I.

As used herein, the terms "host," "subject" and "patient" refer to any animal, including but not limited to, human and non-human animals (e.g., dogs, cats, cows, horses, sheep, poultry, fish, crustaceans, etc.) that is studied, analyzed, tested, diagnosed or treated. As used herein, the terms "host," "subject" and "patient" are used interchangeably, unless indicated otherwise.

As used herein, the terms "subject at risk of cancer" refers to a subject identified as being at risk for developing cancer, e.g., by prior health history, genetic data, etc.

As used herein, the term "anticancer drug" refers to an agent used to treat or prevent cancer. Such agents include, but are not limited to, small molecules, drugs, antibodies, pharmaceuticals, and the like.

As used herein, the terms "subject having depression" or "subject displaying signs or symptoms or pathology indicative of depression" or "subjects suspected of displaying signs or symptoms or pathology indicative of depression" refer to a subject that is identified as having or likely to have depression based on known depression signs, symptoms and pathology.

As used herein, the terms "subject at risk of displaying pathology indicative of depression" and "subject at risk of depression" refer to a subject identified as being at risk for developing depression.

As used herein, the terms "subject having bipolar disorder" or "subject displaying signs or symptoms or pathology indicative of bipolar disorder" or "subjects suspected of displaying signs or symptoms or pathology indicative of bipolar disorder" refer to a subject that is identified as having or likely to have bipolar disorder based on known depression signs, symptoms and pathology.

As used herein, the terms "subject at risk of displaying pathology indicative of bipolar disorder" and "subject at risk of bipolar disorder" refer to a subject identified as being at risk for developing bipolar disorder.

As used herein, the term "antidepressant" refers to an agent used to treat or prevent depression. Such agents include, but are not limited to, small molecules, drugs, antibodies, pharmaceuticals, and the like.

As used herein, "anxiolytic" refers to an agent used to treat or prevent anxiety. Such agents include, but are not limited to, small molecules, drugs, antibodies, pharmaceuticals, and the like.

As used herein, the terms "subject having anxiety" or "subject displaying signs or symptoms or pathology indicative of anxiety" or "subjects suspected of displaying signs or symptoms or pathology indicative of anxiety" refer to a subject that is identified as having or likely to have anxiety based on known anxiety signs, symptoms and pathology.

As used herein, the terms "subject at risk of displaying pathology indicative of anxiety" and "subject at risk of anxiety" refer to a subject identified as being at risk for developing anxiety.

As used herein, the term "cognitive function" generally refers to the ability to think, reason, concentrate, or remember. Accordingly, the term "decline in cognitive function" refers to the deterioration of lack of ability to think, reason, concentrate, or remember.

As used herein, the term "effective amount" refers to the amount of an active composition (e.g., a pharmaceutical compound or composition provided as a component in a lipid or other formulation) sufficient to produce a selected effect, e.g., to effect beneficial or desired results. For example, an effective amount of a PKC inhibitor is an amount of the inhibitor sufficient to reduce PKC activity, as determined, e.g., by observation of an in vivo effect associated with reduced PKC activity, or by use of an in vitro assay. An effective amount can be administered in one or more administrations, applications or dosages and is not intended to be limited to a particular formulation or administration route.

As used herein, the terms "active" or "pharmaceutically active" as used in reference to an agent, drug, composition, or compound, refers to an agent that, upon administration or application, causes a beneficial, desired, or expected result. The administration may be in one or more administrations, applications or dosages and is not intended to be limited to a particular formulation or administration route. The term is not limited to any particular level of activity.

The terms "agent" and "compound" are used herein interchangeably to refer to any atom, molecule, mixture, or more complex composition having an attributed feature. For example, an "active agent" or "active compound" refers to any atom, molecule, preparation, mixture, etc., that, upon administration or application, causes a beneficial, desired, or expected result.

As used herein, the term "treating" includes administering therapy to prevent, cure, or alleviate/prevent the symptoms associated with, a specific disorder, disease, injury or condition.

As used herein, the term "treatment" or grammatical equivalents encompasses the improvement and/or reversal of the symptoms of disease (e.g., cancer, bipolar disorder, Parkinson's disease, etc.), or reduction of risk of occurrence of disease. A compound which causes an improvement in any parameter associated with disease when used in the screening methods of the instant invention may thereby be identified as a therapeutic compound. The term "treatment" refers to both therapeutic treatment and prophylactic or preventative measures. For example, those who may benefit from treatment with compositions and methods of the present invention include those already with a disease and/or disorder (e.g., cancer, psychiatric or neurodegenerative disease, or symptoms or pathologies consistent with these conditions) as well as those in which a disease and/or disorder is to be prevented (e.g., using a prophylactic treatment of the present invention).

As used herein, the term "at risk for disease" refers to a subject (e.g., a human) that is predisposed to experiencing a particular disease. This predisposition may be genetic (e.g., a particular genetic tendency to experience the disease, such as heritable disorders), or due to other factors (e.g., age, weight, environmental conditions, exposures to detrimental compounds present in the environment, etc.). Thus, it is not intended that the present invention be limited to any particular risk, nor is it intended that the present invention be limited to any particular disease.

As used herein, the term "suffering from disease" refers to a subject (e.g., a human) that is experiencing a particular disease. It is not intended that the present invention be limited to any particular signs or symptoms, nor disease. Thus, it is intended that the present invention encompasses subjects that are experiencing any range of disease (e.g., from sub-clinical manifestation to full-blown disease) wherein the subject exhibits at least some of the indicia (e.g., signs and symptoms) associated with the particular disease.

As used herein, the terms "disease" and "pathological condition" are used interchangeably to describe a state, signs, and/or symptoms that are associated with any impairment of the normal state of a living animal or of any of its organs or tissues that interrupts or modifies the performance of normal functions, and may be a response to environmental factors (such as emotional trauma, physical trauma, malnutrition, industrial hazards, or climate), to specific infective agents (such as worms, bacteria, or viruses), to inherent defect of the organism (such as various genetic anomalies, or to combinations of these and other factors.

As used herein, the term "administration" refers to the act of giving a drug, prodrug, or other active agent, or therapeutic treatment (e.g., compositions of the present invention) to a physiological system (e.g., a subject or in vivo, in vitro, or ex vivo cells, tissues, and organs). Exemplary routes of administration to the human body can be through the eyes (ophthalmic), mouth (oral), skin (transdermal), nose (nasal), lungs (inhalant), rectal, vaginal, oral mucosa (buccal), ear, by injection (e.g., intravenously, subcutaneously, intratumorally, intraperitoneally, etc.) and the like. Administration may be in one or more administrations, applications or dosages, and is not intended to be limited to a particular administration route.

As used herein, the term "co-administration" refers to the administration of at least two agent(s) (e.g., two separate lipid compositions, containing different active compounds) or therapies to a subject. For example, in some embodiments, endoxifen may be co-administered with a second therapeutic, e.g., a known therapeutic for the treatment of a disease or condition, e.g., depression. In some embodiments, the co-administration of two or more agents or therapies is concurrent. In other embodiments, a first agent/therapy is administered prior to a second agent/therapy. Those of skill in the art understand that the formulations and/or routes of administration of the various agents or therapies used may vary. The appropriate dosage for co-administration can be readily determined by one skilled in the art. In some embodiments, when agents or therapies are co-administered, the respective agents or therapies are administered at lower dosages than appropriate for their administration alone. Thus, co-administration is especially desirable in embodiments where the co-administration of the agents or therapies lowers the requisite dosage of a potentially harmful (e.g., toxic) agent(s).

A "known therapeutic" compound or agent includes a therapeutic compound that has been shown (e.g., through animal trials or prior experience with administration to humans) to have a particular therapeutic effect in a treatment. However, a known therapeutic compound is not limited to a compound having a particular level of effectiveness in the treatment or prevention of a disease (e.g., bipolar disorder, depression or anxiety). Examples of known bipolar disorder therapeutic agents include but are not limited to lithium, including salts available under the generic names of lithium carbonate and lithium citrate (e.g., ESKALITH, LITHOBID, LITHANE, LITHONATE, LITHOTABS, CIBALITH-S), and anticonvulsants such as valproate or valproic acid (DEPAKOTE), lamotrigine (LAMICTAL), carbamazepine (TEGRETOL), and oxcarbazepine (TRILEPTAL). Examples of other compounds also finding use in combination with endoxifen in the methods of the invention include gabapentin (NEUROTONIN) and topiramate (TOPAMAX). Known antidepressant therapeutic agents that find use include, but are not limited to, selective serotonin reuptake inhibitors (SSRIs, e.g., citalopram (CELEXA), escitalopram (LEXAPRO), fluoxetine (PROZAC, PROZAC WEEKLY), paroxetine (PAXIL, PAXIL CR) and sertraline (ZOLOFT); serotonin and norepinephrine reuptake inhibitors (SNRIs, e.g., duloxetine (CYMBALTA) and venlafaxine (EFFEXOR, EFFEXOR XR); norepinephrine and dopamine reuptake inhibitors (NDRIs, e.g., bupropion (WELLBUTRIN, WELLBUTRIN SR, WELLBUTRIN XL); tetracyclic antidepressants (e.g., mirtazapine (REMERON, REMERON SOLTAB); combined reuptake inhibitors and receptor blockers (e.g., trazodone, tefazodone, maprotiline); tricyclic antidepressants (TCAs, e.g., amitriptyline, amoxapine, desipramine (NORPRAMIN), doxepin (SINEQUAN), imipramine (TOFRANIL), nortriptyline (PAMELOR), protriptyline (VIVACTIL), trimipramine (SURMONTIL)); monoamine oxidase inhibitors (MAOIs, e.g., phenelzine (NARDIL), tranylcypromine (PARNATE), isocarboxazid (MARPLAN), and selegiline (EMSAM)). Examples of known anxiolytic therapeutic agents include, but are not limited, benzodiazepines (e.g., diazepam (VALIUM), nitrazepam (MOGADON), alprazolam (XANAX), bromazepam (LEXOTAN), chlordiazepoxide (LIBRIUM), chlorazepate (TRANXENE), lorazepam (ATIVAN), oxazepam, flunitrazepam (ROHYPNOL), flurazepam (DALMANE), loprazolam, lormetazepam, and temazepam); non-benzodiazepine agents (e.g., buspirone (BUSPAR), beta-blockers, and meprobamate (EQUAGESIC)); and non-benzodiazepine hypnotics (e.g., zalepon (SONATA), zolpidem (STILLNOCT), zopiclone (ZIMOVANE), chloral hydrate, triclofos, and clomethizole, aripiprazole (ABILIFY), quetiapine fumarate (SEROQUEL), olanzapine (ZYPREXA), ziprasidone (GEODON), etc.

As used herein, the term "toxic" refers to any detrimental or harmful effects on a subject, a cell, or a tissue as compared to the same cell or tissue prior to the administration of the toxicant.

As used herein, the term "pharmaceutically purified" refers to a composition of sufficient purity or quality of preparation for pharmaceutical use.

As used herein, the term "purified" refers to a treatment of a starting composition to remove at least one other component (e.g., another component from a starting composition (e.g., plant or animal tissue, an environmental sample etc.), a contaminant, a synthesis precursor, or a byproduct, etc.), such that the ratio of the purified component to the removed component is greater than in the starting composition.

As used herein, the term "pharmaceutical composition" refers to the combination of an active agent (e.g., an active pharmaceutical compound) with a carrier, inert or active (e.g., a phospholipid), making the composition especially suitable for diagnostic or therapeutic use in vitro, in vivo or ex vivo.

The terms "pharmaceutically acceptable" or "pharmacologically acceptable," as used herein, refer to compositions that do not substantially produce adverse reactions, e.g., toxic, allergic, or immunological reactions, when administered to a subject.

As used herein, the term "topically" refers to application of the compositions of the present invention to the surface of the skin and mucosal cells and tissues (e.g., alveolar, buccal, lingual, masticatory, or nasal mucosa, and other tissues and cells which line hollow organs or body cavities).

As used herein, the term "pharmaceutically acceptable carrier" refers to any of the standard pharmaceutical carriers including, but not limited to, phosphate buffered saline solution, water, emulsions (e.g., such as an oil/water or water/oil emulsions), and various types of wetting agents, any and all solvents, dispersion media, coatings, sodium lauryl sulfate, isotonic and absorption delaying agents, disintegrants (e.g., potato starch or sodium starch glycolate), and the like. The compositions also can include stabilizers and preservatives. For examples of carriers, stabilizers, and adjuvants. (See e.g., Martin, Remington's Pharmaceutical Sciences, 15th Ed., Mack Publ. Co., Easton, Pa. (1975), incorporated herein by reference). Moreover, in certain embodiments, the compositions of the present invention may be formulated for horticultural or agricultural use. Such formulations include dips, sprays, seed dressings, stem injections, sprays, and mists.

As used herein, the term "pharmaceutically acceptable salt" refers to any salt (e.g., obtained by reaction with an acid or a base) of a compound of the present invention that is physiologically tolerated in the target subject (e.g., a mammalian subject, and/or in vivo or ex vivo, cells, tissues, or organs). "Salts" of the compounds of the present invention may be derived from inorganic or organic acids and bases. Examples of acids include, but are not limited to, hydrochloric, hydrobromic, sulfuric, nitric, perchloric, fumaric, maleic, phosphoric, glycolic, lactic, salicylic, succinic, toluene-p-sulfonic, tartaric, acetic, citric, methanesulfonic, ethanesulfonic, formic, benzoic, malonic, sulfonic, naphthalene-2-sulfonic, benzenesulfonic acid, and the like. Other acids, such as oxalic, while not in themselves pharmaceutically acceptable, may be employed in the preparation of salts useful as intermediates in obtaining the compounds of the invention and their pharmaceutically acceptable acid addition salts.

Examples of bases include, but are not limited to, alkali metal (e.g., sodium) hydroxides, alkaline earth metal (e.g., magnesium) hydroxides, ammonia, and compounds of formula $NW_4^+$, wherein W is $C_{1-4}$ alkyl, and the like.

Examples of salts include, but are not limited to: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, flucoheptanoate, glycerophosphate, hemisulfate, heptanoate, hexanoate, chloride, bromide, iodide, 2-hydroxyethanesulfonate, lactate, maleate, methanesulfonate, 2-naphthalenesulfonate, nicotinate, oxalate, palmoate, pectinate, persulfate, phenylpropionate, picrate, pivalate, propionate, succinate, tartrate, thiocyanate, tosylate, undecanoate, and the like. Other examples of salts include anions of the compounds of the present invention compounded with a suitable cation such as $Na^+$, $NH_4^+$, and $NW_4^+$ (wherein W is a $C_{1-4}$ alkyl group), and the like. For therapeutic use, salts of the compounds of the present invention are contemplated as being pharmaceutically acceptable. However, salts of acids and bases that are non-pharmaceutically acceptable may also find use, for example, in the preparation or purification of a pharmaceutically acceptable compound.

For therapeutic use, salts of the compounds of the present invention are contemplated as being pharmaceutically acceptable. However, salts of acids and bases that are non-pharmaceutically acceptable may also find use, for example, in the preparation or purification of a pharmaceutically acceptable compound.

As used herein, the term "hydroalcoholic" as used in reference to a substance or composition indicates that said substance or composition comprises both water and alcohol.

As used herein, the term "gelling agent" refers to a composition that, when dissolved, suspended or dispersed in a fluid (e.g., an aqueous fluid such as water or a buffer solution), forms a gelatinous semi-solid (e.g., a lubricant gel). Examples of gelling agents include but are not limited to hydroxyethyl cellulose, hydroxymethyl cellulose, hydroxypropyl guar, methyl cellulose, ethyl cellulose, hydroxypropyl cellulose, sodium carboxymethyl cellulose, carbomer, alginate, gelatin, and poloxamer.

As used herein, the term "dried" as used in reference to a composition refers to removing the solvent component or components to levels that no longer support chemical reactions. The term is also used in reference to a composition that has been dried (e.g., a dried preparation or dried composition). Those of skill in the art will appreciate that a composition may be "dried" while still having residual solvent or moisture content after, e.g., lyophilization, or that a dried composition may, after the end of a drying process, absorb moisture hygroscopically, e.g., from the atmosphere. The term "dried" encompasses a composition with increased moisture content due to hygroscopic absorption.

As used herein, the term "protective agent" refers to a composition or compound that protects the activity or integrity of an active agent (e.g., an anticancer drug or a psychiatric or neurodegenerative disease drug) when the active agent is exposed to certain conditions (e.g., drying, freezing). In some embodiments, a protective agent protects an active agent during a freezing process (i.e., it is a "cryoprotectant"). Examples of protective agents include but are not limited to non-fat milk solids, trehalose, glycerol, betaine, sucrose, glucose, lactose, dextran, polyethylene glycol, sorbitol, mannitol, poly vinyl propylene, potassium glutamate, monosodium glutamate, Tween 20 detergent, Tween 80 detergent, and an amino acid hydrochloride.

As used herein, the term "excipient" refers to an inactive ingredient (i.e., not pharmaceutically active) added to a preparation of an active ingredient. The gelling and protective agents described herein may be referred to generally as "excipients."

As used herein, the term "kit" refers to any delivery system for delivering materials. In the context of kinase activity or inhibition assays, such delivery systems include systems that allow for the storage, transport, or delivery of reaction reagents and/or supporting materials (e.g., buffers, written instructions for performing the assay etc.) from one location to another. For example, kits include one or more enclosures (e.g., boxes) containing the relevant reaction reagents and/or supporting materials. As used herein, the term "fragmented kit" refers to delivery systems comprising two or more separate containers that each contains a sub-portion of the total kit components. The containers may be delivered to the intended recipient together or separately. For example, a first container may contain an agent for use in an assay, while a second container contains standards for comparison to test compounds. The term "fragmented kit" is intended to encompass kits containing Analyte Specific Reagents (ASR's) regulated under section 520(e) of the Federal Food, Drug, and Cosmetic Act, but are not limited thereto. Indeed, any delivery system comprising two or more separate containers that each contains a subportion of the total kit components are included in the term "fragmented kit." In contrast, a "combined kit" refers to a delivery system containing all of the components of a reaction assay in a single container (e.g., in a single box housing each of the desired components). The term "kit" includes both fragmented and combined kits.

DETAILED DESCRIPTION OF THE INVENTION

The present invention provides medical uses for compositions containing endoxifen. This invention further relates to endoxifen and compositions comprising endoxifen in the treatment of psychiatric and neurodegenerative diseases. In particular, the present invention relates to the use of compositions comprising endoxifen in the treatment of bipolar disease, schizophrenia, multiple sclerosis (MS), Alzheimer disease, Parkinson disease, Huntington's disease, amyotrophic lateral sclerosis (ALS), and epilepsy. The invention still further relates to methods of preparing endoxifen and use of endoxifen prepared by inventive method in the treatment of human and animal diseases.

Figure 3:
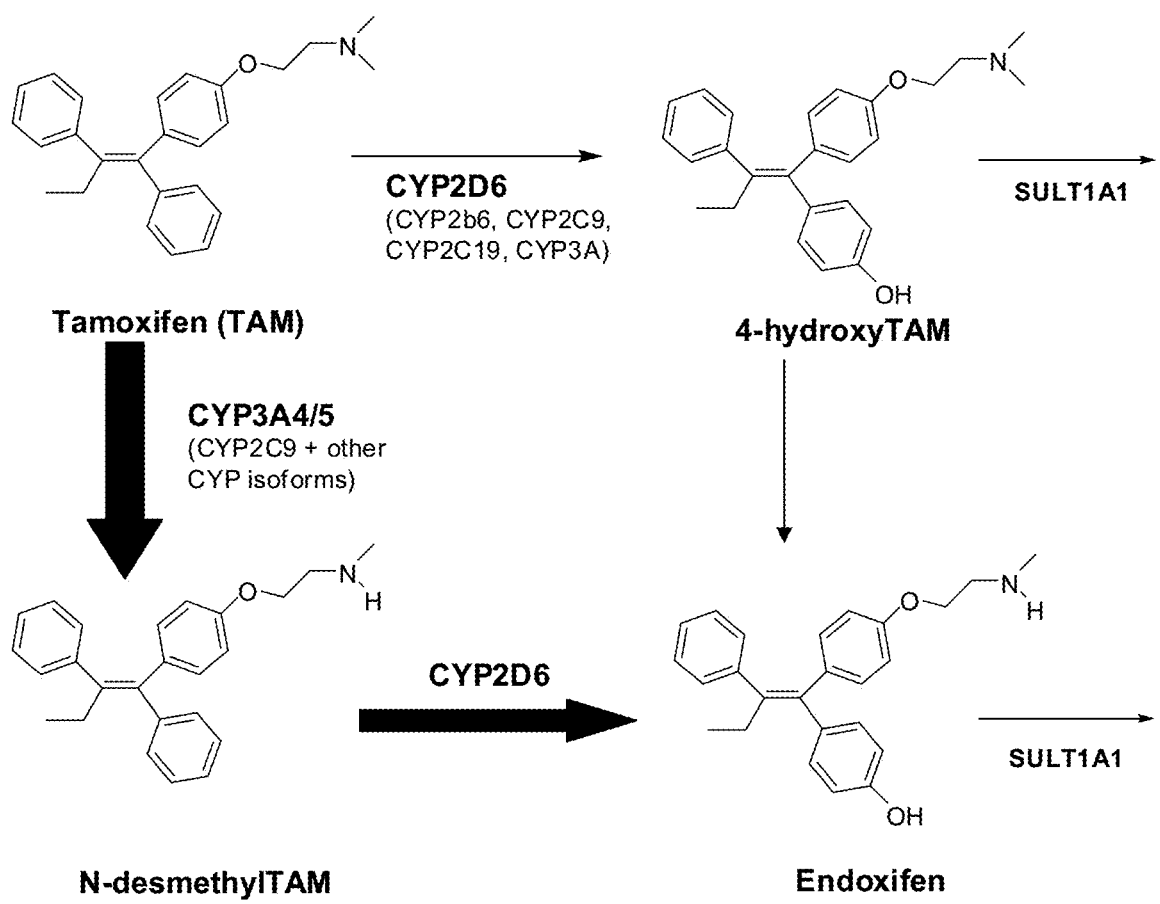
FIG. 3 shows a schematic diagram of metabolism of tamoxifen into endoxifen (4-hydroxy-N-desmethyl tamoxifen).

Endoxifen is generated via CYP3A4-mediated N-demethylation and CYP2D6 mediated hydroxylation of tamoxifen (see, e.g., FIG. 3). As is discussed above, it is well known that co-administration of tamoxifen with drugs that inhibit paroxetine decreases the plasma concentration of endoxifen (5). In addition, any drug that can be substrate of CYP3A4 or CYP2D6 (e.g., SSRIs), even if not an inhibitor of theses drug metabolizing enzymes, can decrease the serum level of endoxifen (5) and thus reduce the therapeutic benefits of tamoxifen. It is therefore advised that, to avoid such drug-drug interactions, one should not give them together.

Recently, endoxifen has been shown to be anti-estrogenic in breast cancer cells and to be more potent than tamoxifen. In patients treated with tamoxifen, endoxifen is present in higher concentration (12.4 ng/mL) than 4-OH-tamoxifen (1 ng/mL) in the human plasma. The majority of genes affected by endoxifen are estrogen-regulated genes (15, 16). Use of endoxifen e.g., in place of tamoxifen, avoids several metabolic steps that rely on CYP2D6.

We have found that endoxifen inhibits PKC and thus finds use in the treatment of psychiatric and neurodegenerative diseases, e.g. in the treatment of bipolar disorder. While not limiting the invention to any particular mode or mechanism of action, the effects observed are consistent with the observation that lithium and valproate, the most commonly used treatments for bipolar disorder, are known to provide the therapeutic effect via attenuation of PKC activity.

Use of Endoxifen in Psychiatric and Neurodegenerative Diseases

ENDOXIFEN (4-hydroxy N-desmethyl tamoxifen) is an active metabolite of the marketed drug tamoxifen for the treatment of breast cancer. Tamoxifen is extensively metabolized by cytochrome P450 (CYP) enzymes CYP3A4 and CYP2D6 into active metabolites including 4-hydroxy tamoxifen and 4-hydroxy-N-desmethyl tamoxifen (endoxifen) (FIG. 1).We hypothesize that endoxifen will have beneficial effect in Bipolar disorder, Schizophrenia and neuroprotective role in Multiple Sclerosis, Parkinson disease, Alzheimer disease, Huntington disease, Amyotrophic Lateral Sclerosis, and Epilepsy. The use of endoxifen as a therapeutic agent for psychiatric and neurodegenerative diseases will have a significant advantage over the mother compound tamoxifen which requires metabolic activation by cytochrome P450 (CYP) enzymes whose actions are variable because of genetic polymorphism and inhibition via drug-drug interaction.

Psychiatric Diseases

Bipolar Disorder

Bipolar disorder is a chronic mental illness that is associated with a substantial risk of suicide among those affected (8). Lithium and valproate are widely used as mood stabilizers in bipolar disorder, however, a substantial minority of patients fails to respond, or respond only partially, to these agents (8). Therefore, the development of novel therapeutic agents with a quicker, more potent, and more specific mode(s) of action with fewer side effects are required.

Figure 4:
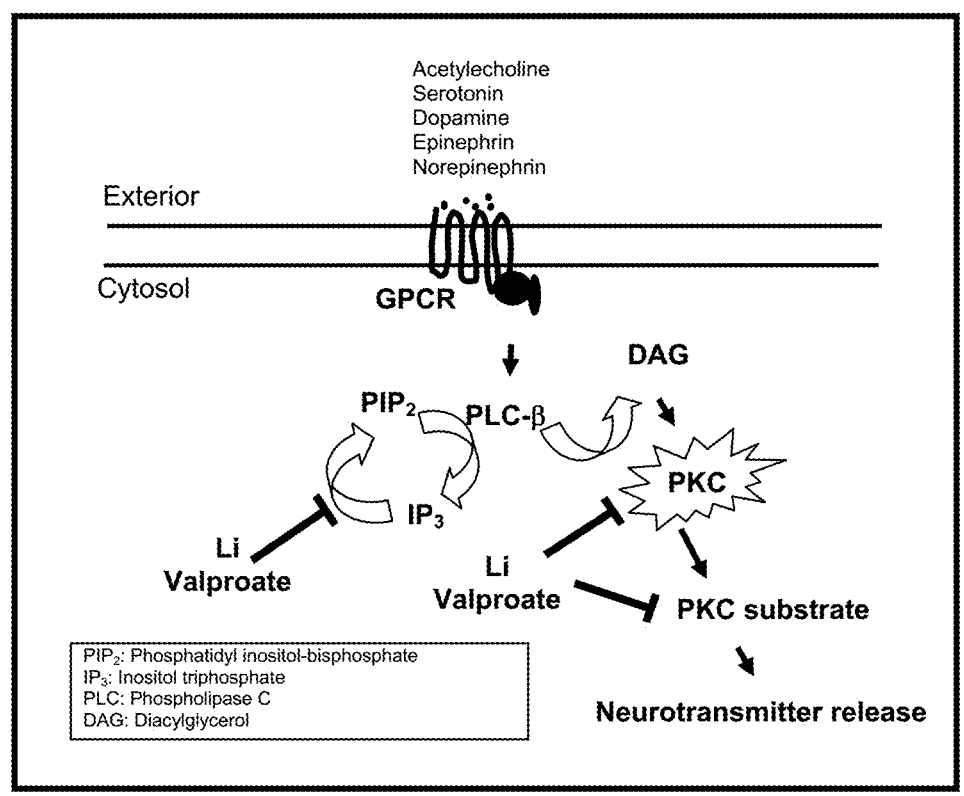
FIG. 4 shows a schematic representation of a PKC pathway.

While precise mechanisms of the disease pathophysiology is not clear, role of Protein kinase C (PKC) signaling pathways has also been implicated in bipolar disorder (17). PKC plays a major role in regulating both pre and postsynaptic neurotransmission. Thus, it is likely that variation in PKC activity causing cellular signaling changes in the brain results in mood swing, such as variation in motor, cognitive and psychological behavior. Animal studies data suggest that excessive PKC activation can disrupt regulation of behavior, possibly contributing to such dysfunctions as distractibility, impaired judgment, impulsivity, and disorganized thought disorder, all of which are characteristic of patients with bipolar disorder (9, 17). These preclinical findings strongly suggest that PKC signaling in the brain represents a highly plausible target for mood-stabilizing drugs (17). Most widely used mood stabilizers such as lithium and valproate are also known to impart pharmacotherapeutic action via alleviation of PKC activity either directly or through their action on PKC substrate Myristoylated alanine-rich C kinase substrate (MARCKS) (17) (FIG. 4).

Tamoxifen is the only compound with documented and appreciable central nervous system (CNS) PKC inhibitory activity that can be administered peripherally and has been approved for human. In a recent study in rats, tamoxifen attenuated amphetamine-induced manic behavior (9). These results support the possibility that PKC signaling may play an important role in the pathophysiology and treatment of bipolar disorder. These findings have direct clinical implications as they offer a new avenue for attempts to develop more specific drugs for the disorder. A preliminary double-blind, controlled clinical trial showed greater antimanic effects with tamoxifen than with placebo (18). More recently two groups have convincingly confirmed in double-blind, placebo controlled studies that PKC inhibitor tamoxifen demonstrated antimanic properties and was well tolerated (10, 11). These findings encourage development of tamoxifen and its metabolites, such as endoxifen as potential antimanic or mood-stabilizing agents.

Schizophrenia

Schizophrenia is a mental illness characterized by episodic symptoms such as delusions, hallucinations, paranoia and psychosis and may include persistent symptoms such as flattened affect, impaired attention, social withdrawal and cognitive impairment (19). Epidemiologic and clinical evidence suggests an influence of estrogens on incidence and enormity of schizophrenia. Although early studies suggested the incidence of schizophrenia in men and women was about equal more recent studies indicate incidence rates are higher in men (20).

Estrogen acts as a protective factor in women; the age of onset of schizophrenia is significantly later in women than in men, with a second peak of onset larger and later in women after 40-45 years of age. Furthermore, levels of psychopathology fluctuate with phases of the menstrual cycle (21). In women with schizophrenia, relapse rates are higher when estrogen levels are low during the menstrual cycle, whereas relapse is low when estrogen levels are high (22). Higher rates of relapse in women with schizophrenia are also observed during the postpartum period (low estrogens), whereas relapse is low during pregnancy (high estrogens). On the other hand, men with schizophrenia have an earlier age of onset, are admitted to hospital earlier and demonstrate a more typical picture and poorer prognosis than women.

Evidence supporting the psychotherapeutic effects of exogenous estrogen in schizophrenia has emerged through the findings of three, double-blind, randomized controlled clinical trials exploring hormone modulation in premenopausal woman with schizophrenia, who received adjunctive transdermal estradiol, in postmenopausal women with schizophrenia on adjunctive raloxifene, a SERM, and in women with schizoaffective disorder, in the manic phase, who received tamoxifen (12). The results showed that adjunctive estradiol was associated with an improvement in symptoms of psychosis in a premenopausal woman with schizophrenia; adjunctive raloxifene was associated with an improvement in cognitive functioning in a postmenopausal woman with schizophrenia; and adjunctive tamoxifen was associated with an improvement in symptoms of mania in a woman with schizoaffective disorder. These findings suggest that adjunctive hormone modulation with SERMs such as tamoxifen is a promising area of gender-specific treatment for schizophrenia.

Neurodegenerative

Multiple Sclerosis

Multiple sclerosis (MS) is an autoimmune disease of the CNS in which the immune system mounts an inappropriate response to components of myelin, such as myelin basic protein or proteolipid protein. It is characterized by inflammation of the CNS and myelin damage. Autoreactive $CD4^+$ T-helper-1 (Th1) cells and their products (for example, tumor necrosis factor-$\alpha$ (TNF-$\alpha$), interferon$\gamma$ (IFN-$\gamma$), and metalloproteinases) mediate much of the immunopathology, resulting in the destruction of the myelin sheath and subsequent neurological dysfunction (23).

Like other autoimmune diseases, the incidence of MS is higher (2 to 3 times) in females compared with males (24) attributing this to hormonal influences. The disease modulating effects of estrogens in MS have been described extensively (25). In both MS patients and animal disease models the protective effects of estrogens have been well documented. These findings suggest that the protective effect on the disease process may be due, at least in part, to modulation of the immune response by estrogens. However, the risks and side effects associated with steroidal estrogens may limit their usefulness for long-term MS therapy.

Selective estrogen receptor modulators could provide an alternative therapeutic strategy, because they behave as estrogen agonists in some tissues, but are either inert or behave like estrogen antagonists in other tissues (26). For example, raloxifene, a SERM that is approved for the treatment of osteoporosis, behaves as an estrogen in bone, whereas it acts as an estrogen antagonist in breast tissue and in the uterus (27). In a more recent study, the ability of tamoxifen and raloxifene to regulate myelin specific immunity and EAE in mice was investigated. Both tamoxifen and raloxifene suppressed myelin antigen specific T-cell proliferation. However, tamoxifen was more effective in this regard. These findings support the notion that tamoxifen or related SERMs are potential agents that could be used in the treatment of inflammatory autoimmune disorders of the CNS such as MS (28).

Alzheimer Disease

Alzheimer disease is one of the most common neurodegenerative disorders and the most common form of dementia in the elderly. Estrogen appears possess a protective role in the prevention of Alzheimer disease. It may exert several neuroprotective effects on the aging brain, including inhibition of β-amyloid plaque formation, stimulation of cholinergic activity, reduction of oxidative stress-related cell damage, and protection against vascular risk. Post-menopausal hormone replacement therapy reduces the risk of developing dementia by approximately 30%. Likewise, patients on raloxifene for osteoporosis had a 33% reduction in risk of mild cognitive impairment and half the relative risk of developing Alzheimer disease, suggesting SERMs' role in prevention of age-related neurodegenerative disorders (29). Investigation of tamoxifen (and its metabolite, 4-hydroxytamoxifen) in an in vitro neuronal model system suggests that this agent could act as a partial agonist in the brain to provide some neuroprotective benefit after the menopause (14).

Parkinson Disease

Parkinson disease (PD) is another common degenerative disorder characterized by selective loss of dopaminergic neurons in the substantia nigra of the midbrain leading to depletion of dopamine (30). Normal dopamine transmission can be restored by the administration of pharmacological agents, levodopa or dopamine agonists. After prolonged administration, adverse motor complications eventually appear including motor fluctuations and dyskinesias. Protein kinase C may accelerate the onset of levodopa-associated motor changes (31). Tamoxifen could act as a PKC antagonist and in rats and non-human primates reverses the shortening of beneficial response of chronic levodopa therapy (32). Similarly, tamoxifen co-administered with levodopa to Parkinsonian monkeys significantly attenuated levodopa-induced dyskinesias by 61% (32).

In addition to its action via PKC, tamoxifen has multiple metabolic effects including a neuroprotective function (33). Tamoxifen has also been shown to stimulate dopamine release. Overall, this evidence suggests that tamoxifen may have a role in inhibiting the unwanted motor disorders seen with chronic levodopa administration in PD and possibly have a role in chemoprevention of neurodegenerative disorders.

The present invention provides compositions and methods for delivering endoxifen of Formula I, e.g., to a mammalian host. In some embodiments of the present invention endoxifen is an E-isomer, while in other embodiments, it is a Z-isomer, while it is still in other embodiments, it is a mixture of E- and Z-isomers

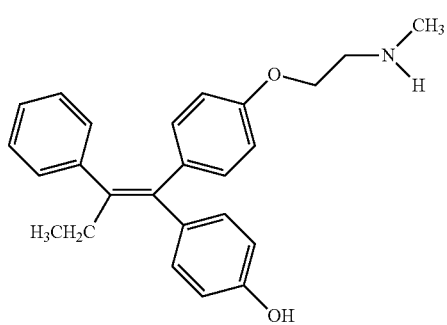

I

An example of the present invention includes endoxifen, analogues of endoxifen, and derivatives of endoxifen, including but not limited to endoxifen, tamoxifen, and 4-hydroxytamoxifen. The present invention also find use with other antineoplastic agents such as paclitaxel, docetaxel, melphalan, chlormethine, extramustinephosphate, uramustine, ifosfamide, mannomustine, trifosfamide, streptozotocin, mitobronitol, mitoxantrone, methotrexate, fluorouracil, cytarabine, tegafur, idoxide, taxol, paclitaxel, daunomycin, daunorubicin, bleomycin, amphotericin, carboplatin, cisplatin, BCNU, vincristine, camptothecin, SN-38, doxorubicin, and etopside. Also included are steroidal and non-steroidal inhibitors used in cancer treatment, such as bicautamide, exemestane, formestane, letrozole, anastrazole and their analogues.

Figure 2:
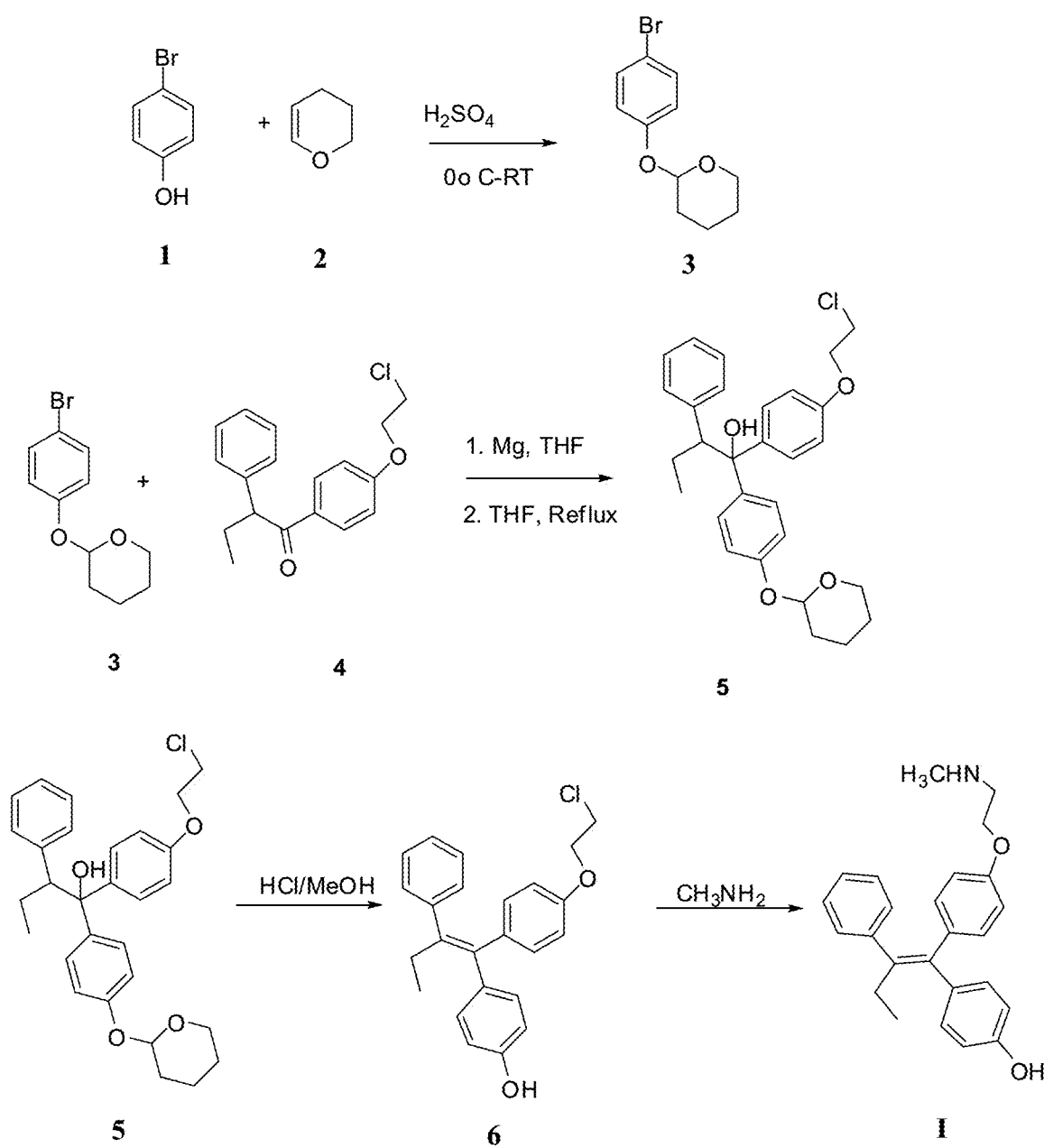
FIG. 2 diagrams embodiments for synthesis of compounds 3, 5, and I.

Endoxifen of Formula I can be prepared by any desired method for use in the treatments of the present invention but, in some embodiments, the present invention provides particular methods for the preparation of endoxifen. One preferred method of the present invention is set forth in FIG. 2. In this method, 4-bromophenol 1 is reacted with 3,4-dihydropyran 2 in the present of acid (e.g., sulfuric acid and the like), to give compound 3. Compound 3 is then reacted with magnesium turning in a suitable anhydrous solvent (e.g., tetrahydrofuran and the like). This is followed by reaction with 1-[4-(2-chloroethoxy) phenyl]-2-phenyl-1-butanone 4 to provide compound 5 which, on dehydration/deprotection in presence of acid in a suitable solvent (e.g., methanol and the like), produces compound 6. Reaction of yielded compound 6 with methylamine in a suitable solvent (e.g., isopropanol and the like) provides endoxifen I.

In some embodiments of the present invention, a mixture of E- and Z-isomers of endoxifen can be separated to provide the purified preparations of E- and Z-isomer of endoxifen. The separation of E- and Z-isomers of endoxifen in the present invention can be done, e.g., by crystallization, or purification by liquid column chromatography (LC), or high pressure liquid column chromatography (HPLC).

Suitable solvents that can be employed in present invention for the separation of E- and Z-isomers of endoxifen include but are not limited to hexanes, heptanes, and the like, benzene; toluene; ethyl acetate; acetonitrile; chlorinating solvents such as methylene chloride, chloroform, 1,2-dichloromethane, and the like, ketones, (e.g., acetone, 2-butanone, and the like), ethers such as diethyl ether, diisopropyl ether, methyl butyl ether, and tetrahydrofuran, alcohols such as methanol, ethyl alcohol, and isopropyl alcohol, and the like, and water. A solvent for crystallization can be used as a single solvent, or as mixture of solvents such as hexane-ethyl acetate, chloroform-acetone, chloroform-methanol, dichloromethane-methanol, and the like. When a mixture of two solvents is used in the present invention, examples of ratios of one solvent to another are e.g., in a range such as 9:1 to 1:9, (e.g., 8:2, 7:3; 6:4; 5:5; 4:6; 3:7; 2:8; 1:9, and the like.) However, mixtures for use in the present invention are not limited to these ratios, or to mixtures comprising only two solvents.

Solvents that find use in the preparation of endoxifen according to the present invention include but are not limited to tetrahydrofuran, dichloromethane, chloroform, 1,2-dichloroethane, acetonitrile, N,N'-dimethylformamide, dimethylsulfoxide, toluene, pyridine, methanol, ethanol, isopropanol, acetone, 2-butanone, hexane, heptane, pentane, ethyl acetate, and the like.

Acids that find use in the preparation of endoxifen according to the present invention include, but are not limited to, sulfuric acid, hydrochloric acid, acetic acid, trifluroacetic acid, phosphoric acid, p-toluenesulfonic acid, methanesulfonic acid, nitric acid, and the like.

Intermediates and final products of the present invention can be purified by column chromatography using a single or a mixture of common organic solvents such as hexane pentane, heptane, ethyl acetate, methylene chloride, chloroform, methanol, acetone, and the like.

As noted above, intermediates and final product of the present invention, may, in some embodiments, be purified by crystallization. Solvents that find use in the crystallization of intermediates and products include but are not limited to hydrocarbons such as pentanes, hexanes, heptanes, and the like, benzene; toluene; ethyl acetate; acetonitrile; chlorinating solvents such as methylene chloride, chloroform, 1,2-dichloromethane, and the like; ketones, for example, acetone, 2-butanone, and the like; ethers such as diethyl ether, diisopropyl ether, methyl butyl ether, tetrahydrofuran; alcohols such as methanol, ethyl alcohol, isopropyl alcohol, and the like. A solvent for crystallization can be used as a single solvent or mixture of solvents. Exemplary mixtures include, e.g., hexane-ethyl acetate, chloroform-acetone, chloroform-methanol, dichloromethane-methanol, and the like. When a mixture of two solvents is used in the present invention, examples of ratios of one solvent to another are e.g., in a range such as 9:1 to 1:9, (e.g., 8:2, 7:3; 6:4; 5:5; 4:6; 3:7; 2:8; 1:9, and the like.) However, mixtures for use in the present invention are not limited to these ratios, or to mixtures comprising only two solvents.

One object of the present invention is to provide E-endoxifen or Z-endoxifen with at least 80% purity, such as at least 90% pure or at least 95% pure or at least 98% pure or at least 99% pure or at least 100% pure.

Another object of the present invention is to provide solubilized endoxifen in, e.g., aqueous acid. Suitable acids for solubilizing endoxifen include but are not limited to formic acid, acetic acid, propionic acid, butyric acid, trifluoroacetic acid, lactic acid, tartaric acid, oxalic acid, malonic acid, succinic acid, and the like. The pH of the acidic solution comprising endoxifen can be adjusted with suitable base or buffers. Examples of base and buffers include but are not limited to sodium hydroxide, sodium acetate, sodium lactate, sodium succinate, sodium monophosphate, sodium diphosphate, sodium triphosphate, sodium oxalate, sodium tartarate, ammonium hydroxide, ammonium acetate, and the like. In some embodiments, a co-solvent can also be used to solubilize endoxifen. Examples of co-solvent include but are not limited to ethanol, isopropanol, detergents such as Tween 20 and Polysorbate, and the like In certain preferred embodiments, the pH of a composition containing endoxifen according to the present invention are between about 4.0 and about 8.0, and preferably between about 5.0 and about 8.0, and most preferably between about 5.5 and about 7.5.

In some embodiments, the present invention relates to compositions and methods for delivery of endoxifen or endoxifen-lipid complexes to a mammalian host. Any suitable amount of endoxifen can be used in complex formation. Suitable amounts of endoxifen are those amounts that can be stably incorporated into the complexes of the present invention.

In some embodiments, the inventive composition comprises a lipid complex with endoxifen in which the complex desirably contains lipid or a mixture of lipids. Complexes can be in the form, e.g., of micelles, vesicles or emulsions without exclusion of other forms. The micelles of the present invention can be in the form of monomeric, dimeric, polymeric or mixed micelles. The complexes including micelles and emulsions are predominately in the size range of 50 nm-20 micron, preferably in size range of 50 nm-5 micron. In the complexes, the active agent can be bound to the lipid by covalent, hydrophobic, electrostatic, hydrogen, or other bonds, and is considered bound even where the drug is simply entrapped within the interior of lipid structures.

Endoxifen-lipid complexes may contain e.g., cholesterols or cholesterol derivatives or a mixture of cholesterol and cholesterol derivatives. Cholesterol derivatives that find use in the present invention include cholesteryl hemisuccinate, cholesteryl succinate, cholesteryl oleate, cholesteryl linoleate, cholesteryl eicosapentenoate, cholesteryl linolenate, cholesteryl arachidonate, cholesteryl palmitate, cholesteryl stearate, cholesteryl myristate, polyethylene glycol derivatives of cholesterol (cholesterol-PEG), water soluble cholesterol (for example, cholesterol methyl-β-cyclodextrin), coprostanol, cholastanol, or cholestane, cholic acid, cortisol, corticosterone or hydrocortisone and 7-dehydrocholesterol.

In some preferred embodiments, the compositions also include α-, β-, γ-tocopherols, vitamin E, calciferol, organic acid derivatives of α-, β-, γ-tocopherols, such as α-tocopherol hemisuccinate (THS), α-tocopherol succinate and/or mixtures thereof.

In other some preferred embodiments, endoxifen-lipid complexes of the present invention contain sterols. Sterols that find use in the present invention include β-sitosterol, stigmasterol, stigmastanol, lanosterol, α-spinasterol, lathosterol, campesterol and/or mixtures thereof.

Compositions of the present invention also include endoxifen complexes with free and/or salts or esters of fatty acid. Preferred fatty acids range from those with carbon chain lengths of about $C_2$ to $C_{34}$, preferably between about $C_4$ and about $C_{24}$, and include tetranoic acid ($C_{4:0}$), pentanoic acid ($C_{5:0}$), hexanoic acid ($C_{6:0}$), heptanoic acid ($C_{7:0}$), octanoic acid ($C_{8:0}$), nonanoic acid ($C_{9:0}$), decanoic acid ($C_{10:0}$), undecanoic acid ($C_{11:0}$), dodecanoic acid ($C_{12:0}$), tridecanoic acid ($C_{13:0}$), tetradecanoic (myristic) acid ($C_{14:0}$), pentadecanoic acid ($C_{15:0}$), hexadecanoic (palmatic) acid ($C_{16:0}$), heptadecanoic acid ($C_{17:0}$), octadecanoic (stearic) acid ($C_{18:0}$), nonadecanoic acid ($C_{19:0}$), eicosanoic (arachidic) acid ($C_{20:0}$), heneicosanoic acid ($C_{21:0}$), docosanoic (behenic) acid ($C_{22:0}$), tricosanoic acid ($C_{23:0}$), tetracosanoic acid ($C_{24:0}$), 10-undecenoic acid ($C_{11:1}$), 11-dodecenoic acid ($C_{12:1}$), 12-tridecenoic acid ($C_{13:1}$), myristoleic acid ($C_{14:1}$), 10-pentadecenoic acid ($C_{15:1}$), palmitoleic acid ($C_{16:1}$), oleic acid ($C_{18:1}$), linoleic acid ($C_{18:2}$), linolenic acid ($C_{18:3}$), eicosenoic acid ($C_{20:1}$), eicosdienoic acid ($C_{20:2}$), eicosatrienoic acid ($C_{20:3}$), arachidonic acid (cis-5,8,11,14-eicosatetraenoic acid), and cis-5,8,11,14, 17-eicosapentaenoic acid, among others. Other fatty acids also can be employed in the compositions. Examples of such include saturated fatty acids such as ethanoic (or acetic) acid, propanoic (or propionic) acid, butanoic (or butyric) acid, hexacosanoic (or cerotic) acid, octacosanoic (or montanic) acid, triacontanoic (or melissic) acid, dotriacontanoic (or lacceroic) acid, tetratriacontanoic (or gheddic) acid, pentatriacontanoic (or ceroplastic) acid, and the like; monoethenoic unsaturated fatty acids such as trans-2-butenoic (or crotonic) acid, cis-2-butenoic (or isocrotonoic) acid, 2-hexenoic (or isohydrosorbic) acid, 4-decanoic (or obtusilic) acid, 9-decanoic (or caproleic) acid, 4-dodecenoic (or linderic) acid, 5-dodecenoic (or denticetic) acid, 9-dodecenoic (or lauroleic) acid, 4-tetradecenoic (or tsuzuic) acid, 5-tetradecenoic (or physeteric) acid, 6-octadecenoic (or petroselenic) acid, trans-9-octadecenoic (or elaidic) acid, trans-11-octadecenoic (or vaccinic) acid, 9-eicosenoic (or gadoleic) acid, 11-eicosenoic (or gondoic) acid, 11-docosenoic (or cetoleic) acid, 13-decosenoic (or erucic) acid, 15-tetracosenoic (or nervonic) acid, 17-hexacosenoic (or ximenic) acid, 21-triacontenoic (or lumequeic) acid, and the like; dienoic unsaturated fatty acids such as 2,4-pentadienoic (or β-vinylacrylic) acid, 2,4-hexadienoic (or sorbic) acid, 2,4-decadienoic (or stillingic) acid, 2,4-dodecadienoic acid, 9,12-hexadecadienoic acid, cis-9, cis-12-octadecadienoic (or α-linoleic) acid, trans-9, trans-12-octadecadienoic (or linlolelaidic) acid, trans-10,trans-12-octadecadienoic acid, 11,14-eicosadienoic acid, 13,16-docosadienoic acid, 17,20-hexacosadienoic acid and the like; trienoic unsaturated fatty acids such as 6,10,14-hexadecatrienoic (or hiragonic) acid, 7,10,13-hexadecatrienoic acid, cis-6, cis-9-cis-12-octadecatrienoic (or γ-linoleic) acid, trans-8, trans-10-trans-12-octadecatrienoic (or β-calendic) acid, cis-8, trans-10-cis-12-octadecatrienoic acid, cis-9, cis-12-cis-15-octadecatrienoic (or α-linolenic) acid, trans-9, trans-12-trans-15-octadecatrienoic (or α-linolenelaidic) acid, cis-9, trans-11-trans-13-octadecatrienoic (or α-eleostearic) acid, trans-9, trans-11-trans-13-octadecatrienoic (or β-eleostearic) acid, cis-9, trans-11-cis-13-octadecatrienoic (or punicic) acid, 5,8,11-eicosatrienoic acid, 8,11,14-eicosatrienoic acid and the like; tetraenoic unsaturated fatty acids such as 4,8,11,14-hexadecatetraenoic acid, 6,9,12,15-hexadecatetraenoic acid, 4,8,12,15-octadecatetraenoic (or moroctic) acid, 6,9,12,15-octadecatetraenoic acid, 9,11,13,15-octadecatetraenoic (or α- or β-parinaric) acid, 9,12,15,18-octadecatetraenoic acid, 4,8,12,16-eicosatetraenoic acid, 6,10,14,18-eicosatetraenoic acid, 4,7,10,13-docasatetraenoic acid, 7,10,13,16-docosatetraenoic acid, 8,12,16,19-docosatetraenoic acid and the like; penta- and hexa-enoic unsaturated fatty acids such as 4,8,12,15,18-eicosapentaenoic (or timnodonic) acid, 4,7,10,13,16-docosapentaenoic acid, 4,8,12,15,19-docosapentaenoic (or clupanodonic) acid, 7,10,13,16,19-docosapentaenoic, 4,7,10, 13,16,19-docosahexaenoic acid, 4,8,12,15,18,21-tetracosahexaenoic (or nisinic) acid and the like; branched-chain fatty acids such as 3-methylbutanoic (or isovaleric) acid, 8-methyldodecanoic acid, 10-methylundecanoic (or isolauric) acid, 11-methyldodecanoic (or isoundecylic) acid, 12-methyltridecanoic (or isomyristic) acid, 13-methyltetradecanoic (or isopentadecylic) acid, 14-methylpentadecanoic (or isopalmitic) acid, 15-methylhexadecanoic, 10-methylheptadecanoic acid, 16-methylheptadecanoic (or isostearic) acid, 18-methylnonadecanoic (or isoarachidic) acid, 20-methylheneicosanoic (or isobehenic) acid, 22-methyltricosanoic (or isolignoceric) acid, 24-methylpentacosanoic (or isocerotic) acid, 26-methylheptacosanoic (or isomonatonic) acid, 2,4,6-trimethyloctacosanoic (or mycoceranic or mycoserosic) acid, 2-methyl-cis-2-butenoic(angelic)acid, 2-methyl-trans-2-butenoic (or tiglic) acid, 4-methyl-3-pentenoic (or pyroterebic) acid and the like.

In some preferred embodiments, endoxifen-lipid complexes contain phospholipids. Any suitable phospholipids or mixture of phospholipids can be used. For example, phospholipids can be obtained from natural sources or chemically synthesized. Suitable phospholipids include but are not limited to phosphatidylethanolamine (PE), phosphatidylglycerol (PG), phosphatidylserine (PS), phosphatidylcholine (PC), phosphatidylinositol (PI), phosphatidic acid (PA), sphingomyelin and the like, either used separately or in combination. Phosphatidylglycerols may be having short chain or long chain, saturated or unsaturated such as dimyristoylphosphatidylglycerol, dioleoylphosphatidylglycerol, distearoylphosphatidylglycerol, dipalmitoylphosphatidylglycerol, diarachidonoylphosphatidylglycerol, short chain phosphatidylglycerol ($C_6$-$C_8$), and mixtures thereof. Examples of phosphatidylcholines includes dimyristoylphosphatidylcholine, distearoylphosphatidylcholine, dipalmitoylphosphatidylcholine, dioleoylphosphatidylcholine, diarachidonoylphosphatidylcholine, egg phosphatidylcholine, soy phosphatidylcholine or hydrogenated soy phosphatidylcholine can be used, as can mixtures thereof.

According to one aspect, the present invention provides compositions comprising endoxifen and derivatives of mono-, di- and tri-glycerides. Examples of the glycerides include 1-oleoyl-glycerol (monoolein) and 1, 2-dioctanoyl-sn-glycerol.

Another aspect of the invention provides forming complexes of endoxifen with functionalized phospholipids including but not limited to phosphatidylethanolamine, preferably dioleoylphosphatidylethanolamine, phosphatidylthioethanol, N-biotinylphosphatidylethanolamine and phosphatidylethylene glycol.

Another aspect of the invention provides forming complexes of endoxifen with carbohydrate-based lipids. Examples of carbohydrate-based lipids include but are not limited to galactolipids, mannolipids, galactolecithin and the like.

In other preferred embodiment, endoxifen-lipid complexes comprise sterols. Sterols finding use in the present invention include but are not limited to β-sitosterol, stigmasterol, stigmastanol, lanosterol, α-spinasterol, lathosterol, campesterol and/or mixtures thereof.

Another aspect of the invention provides forming complexes of endoxifen with guggulipid and any suitable phospholipids. Guggulipid, or guggul, is a natural substance derived from the mukul myrrh tree. The mukul myrrh gives off a sticky resin, which is processed to obtain guggulipid. This extract has been used for thousands of years in Aryuvedic medicine to treat arthritis and obesity. The guggulipid is a source of sterol compounds such as Z- and E-guggulsterones, generally present in an amount of at least 2.5% (10). Z and E-Guggulsterones can be synthesized chemically and thus can be used in drug formulations where the need is to have pure forms of these sterones. See, e.g., U.S. Application Ser. No. 60/856,952, filed Nov. 6, 2006, and PCT/US07/83832, filed Nov. 6, 2007, both incorporated herein by reference.

Yet another aspect of the invention provides forming complexes of endoxifen with derivatives of phospholipids such as pegylated phospholipids. Examples of pegylated lipids finding use in the present invention include but are not limited to the polyethylene glycol (Pegylated, PEG) derivatives of distearoylphosphatidylglycerol, dimyristoylphosphatidylglycerol, dioleoylphosphatidylglycerol and the like.

In other aspects, the present invention provides compositions comprising endoxifen and polyethyleneglycol (PEG) and one or more lipids.

According to yet other aspects, the present invention provides compositions comprising endoxifen complexes with one or more lipids. Examples include but are not limited to compositions comprising endoxifen, cholesterol or cholesterol derivatives and one or more phospholipids. Other examples of compositions include endoxifen, β-sitosterol, and one or more phospholipids. In some preferred embodiments, compositions of the present invention comprise endoxifen, and hydrogenated soy phosphatidylcholine or soy phosphatidylcholine.

The term "Polyethylene glycol (PEG)" includes polymers of lower alkylene oxide, in particular ethylene oxide (polyethylene glycols) having an esterifiable hydroxyl group at least at one end of the polymer molecule, as well as derivatives of such polymers having esterifiable carboxy groups. Polyethylene glycols of an average molecular weight ranging from 200-20,000 are preferred; those having an average molecular weight ranging from 500-2000 are particularly preferred.

Another aspect of the invention provides forming complexes of endoxifen with carbohydrate-based lipids. Examples of carbohydrate-based lipids include but are not limited to galactolipids, mannolipids, galactolecithin and the like.

In some embodiments of compositions of the invention, a complex is formed comprising endoxifen and preferably endoxifen in water at a concentration of about 0.5 mg/mL to about 25 mg/mL, such as between 1 mg/mL and about 20 mg/mL or between 1 mg/mL and 10 mg/mL, more preferably between 1 mg/mL and 5 mg/mL.

In some embodiments, compositions of the present invention contain about 2.5% to about 90% of total lipid, preferably about 2.5 to about 50% weight of total lipid or more, preferably about 10% to about 50% weight of total lipid.

In certain embodiments, compositions of the present invention preferably contain endoxifen, and lipid(s) in mole ratio between 1:1 to 1:100 such as in between 1:1 and 1:20 molar ratio or in between 1:1 and 1:30 molar ratio or in between 1:1 and 1:40 molar ratio or in between 1:1 and 1:50 molar ratio, in between 1:1 and 1:60 molar ratio, in between 1:1 and 1:70 molar ratios, and in between 1:1 and 1:80 molar ratios, and 1:90 molar ratios.

Ratios recited herein, e.g., mole ratios of components in a composition, are provided by way of example and do not limit the invention to the precise incremental ratios recited, e.g., to whole number ratios of the components in the composition. For example, a range of ratios of about 1:10 to 1:90 encompasses not only 1:11, 1:25, 1:89, etc., but includes, without limitation, any ratio at or between about 1:10 to 1:90 (e.g., 1:53.637).

In certain embodiments, compositions of the present invention preferably contain endoxifen and hydrogenated soy phosphatidylcholine, or soy phosphatidylcholine, and cholesterol or cholesterol derivative. Such composition includes endoxifen and cholesterol or cholesterol derivative preferably in from about 1:1-1:5 mole ratio, and more preferably at about 1:1 mole ratio to about 1:2 mole ratio.

Yet another aspect of the invention is to form complexes of endoxifen with derivatives of phospholipids, such as pegylated phospholipids. Examples include but are not limited to the polyethylene glycol (PEG) derivatives of distearoylphosphatidylglycerol, dimyristoylphosphatidylglycerol, dioleoylphosphatidylglycerol and the like.

In some preferred embodiments, the mole ratio of endoxifen and hydrogenated soy phosphatidylcholine or soy phosphatidylcholine, in a composition containing endoxifen and hydrogenated soy phosphatidylcholine or phosphatidylcholine is between about 1:10 and 1:90, e.g., between about 1:10 and 1:80 or 1:10 and 1:70 or 1:10 and 1:60 or 1:10 and 1:50 or 1:10 and 1:40 and 1:10 and 1:30. Particularly preferred embodiments, the mole ratio of endoxifen and hydrogenated soy phosphatidylcholine or soy phosphatidylcholine is between 1:10 and 1:60.

In some embodiments, compositions of the present invention preferably contain endoxifen and total lipids having weight to weight ratio between 1:1 to 1:100 ratio such as between 1:1 and 1:20 ratio or between 1:1 and 1:30 ratio or between 1:1 and 1:40 ratio or between 1:1 and 1:50 ratio, or between 1:1 and 1:60 ratio, or between 1:1 and 1:70 ratio, and between 1:1 and 1:80 ratio, or in between 1:1 and 1:90 ratio.

In some embodiments, the method of the present invention comprises solubilizing or suspending endoxifen and lipid(s) together in an aqueous solution, e.g., water. Endoxifen-lipid complex solution can be filtered through suitable filters to control the size distribution of the complexes.

In some embodiments, the method may comprise mixing lipid(s) together in water and then adding endoxifen. Endoxifen-lipid complex solution can be filtered through suitable filters to control the size distribution of the complexes.

In some embodiments, the method also comprises mixing endoxifen and lipid(s) in an organic solvent(s), such as chloroform or ethanol or any other pharmaceutically acceptable solvents, and evaporating the solvent(s) to form a lipid phase or lipid film. The lipid phase is then hydrated with water or an aqueous solution. Examples of aqueous solutions include but are not limited to 0.9% sodium chloride, solutions containing sugars such as dextrose, sucrose, and the like. The hydrated solution can be filtered through suitable filters to control the size distribution of the complexes.

In some embodiments, the method comprises mixing lipid(s) in an organic solvent(s) and evaporating the solvent(s) to form a lipid phase or lipid film. The lipid phase is then hydrated with aqueous solution containing endoxifen. The aqueous solution in addition to endoxifen may further contain sodium chloride or sugars such as dextrose, sucrose and the like. The hydrated solution can be filtered through suitable filters to control the size distribution of the complexes.

In other embodiments, the method of the present invention comprises mixing endoxifen, one or more lipids in any suitable order and in any suitable solvents such that the resulting composition of the present invention contains endoxifen, and one or more lipids.

In some embodiments, the method of preparation of the present invention comprises heating the composition comprising endoxifen, and the lipid(s) at temperatures ranging from 30-100° C. preferably between 30-80° C. and more preferably between 30-60° C.

In some embodiments, the pH of the composition of invention ranges from about 3 to about 11, while a pH between 3.5 to about 8 is preferred and pH of between 4.0 to pH 7.5 are particularly preferred. Aqueous solutions having a particular pH can be prepared from water having comprising appropriate buffers. Preferred buffers include but are not limited to mixtures of monobasic sodium phosphate and dibasic sodium phosphate, tribasic sodium phosphate, disodium succinate. Other buffers that find use with the present invention include sodium carbonate, sodium bicarbonate, sodium hydroxide, ammonium acetate, sodium citrate, tris (hydroxy-methyl) aminoethane, sodium benzoate, and the like.

The mole ratio of endoxifen and hydrogenated soy phosphatidylcholine or soy phosphatidylcholine in the composition containing endoxifen and hydrogenated soy phosphatidylcholine or soy phosphatidylcholine is in between 1:10 and 1:90 such as in between 1:10 and 1:80 or 1:10 and 1:80 or 1:10 and 1:60 or 1:10 and 1:50 or 1:10 and 1:40 and 1:10 and 1:30. In preferred embodiments, the mole ratio of endoxifen and hydrogenated soy phosphatidylcholine or soy phosphatidylcholine is in between 1:5 and 1:60.

As noted above, compositions can be filtered to obtain a desired size range of complexes particle sizes from the filtrate. Filters that find use in the present invention include those that can be used to obtain the desired size range of the complexes from the filtrate. For example, the complexes can be formed and thereafter filtered through a 5 micron filter to obtain complexes, each particle having a diameter of about 5 micron or less. Alternatively, 1 μm, 500 nm, 200 nm, 100 nm or other filters can be used to obtain complexes having diameters of about 1 μm, 500 nm, 200 nm, 100 nm or any suitable size range, respectively.

When desired, the endoxifen-lipid complex can be dried, e.g., by evaporation or lyophilization. In certain embodiments of the invention, the endoxifen-lipid complex can be lyophilized with one or more cryoprotectants such as sugars. In preferred embodiments, sugars include but are not limited to trehalose, maltose, lactose, sucrose, glucose, and dextran. In particularly preferred embodiments, trehalose and/or sucrose are used. Lyophilization is accomplished under vacuum and can take place either with or without prior freezing of the endoxifen lipid preparation. When desired, the complexes can be resuspended in any desirable solvent including water, saline, dextrose and buffer.

Pharmaceutical preparations that find use with the compositions of the present invention include but are not limited to tablets, capsules, pills, dragees, suppositories, solutions, suspensions, emulsions, ointments, and gels. For the oral mode of administration, preferred forms of endoxifen or endoxifen lipid complex include tablets, capsules, lozenges, powders, syrups, aqueous solutions, suspensions and the like. For topical application and suppositories, preferred forms of endoxifen or endoxifen-lipid complex comprise gels, oils, and emulsions, such as are formed by the addition of suitable water-soluble or water-insoluble excipients, for example polyethylene glycols, certain fats, and esters, compounds having a higher content of polyunsaturated fatty acids and derivatives thereof. Derivatives include mono-, di-, and triglycerides and their aliphatic esters (for example, fish oils, vegetable oils etc.) or mixtures of these substances. Suitable excipients are those in which the drug complexes are sufficiently stable to allow for therapeutic use.

When desired, composition containing endoxifen or endoxifen-lipid complex can be encapsulated in enteric-coated capsules to protect it from acids in the stomach. The term "enteric" refers to the small intestine, and enteric coatings prevent release of medication before it reaches the small intestine. Most enteric coatings work by presenting a surface that is stable at acidic pH but breaks down rapidly at higher pH. Enteric coating of capsules filled with composition containing endoxifen or endoxifen-lipid complex can be done as methods known in the art.

The endoxifen-lipid complex of the present invention can be of varying size or can be of substantially uniform size. For example, the complex can have a mean diameter of about 1 mm or less, and more preferably are in the micron or sub-micron range. In some preferred embodiments, the complexes have an average diameter of about 5 µm or less, such as 0.2 µm or less or 0.1 µm or less.

The technology outlined in the present invention may also be used for any other water-insoluble drugs. The methods and compositions of the present invention find use in conjunction with the methods and compositions disclosed in U.S. Application Ser. No. 60/850,446, filed Oct. 10, 2006, PCT Application Ser. No. PCT/US07/80984, filed Oct. 10, 2007, U.S. Application Ser. No. 60/856,952, filed Nov. 6, 2006, PCT Application Ser. No. PCT/US07/83832, filed Nov. 6, 2007, all of which are incorporated by reference herein in their entireties.

The compositions of the present invention can be employed to treat breast cancer and breast related diseases. For example, the compositions of the present invention may be administered to a patient diagnosed with benign breast disease. As used herein, the term "benign breast disease" refers to a constellation of non-malignant aberrations in breast tissue. The aberrations may be proliferative or non-proliferative in nature. The exemplary benign breast diseases treatable by the present inventive compositions include adenosis, cysts, duct ectasia, fibroadenoma, fibrosis, hyperplasia, metaplasia and other fibrocystic changes. Each of these diseases, referred as "changes" or "conditions" due to their prevalence, have well-defined histological and clinical characteristics.

"Adenosis" refers to generalized glandular disease of the breast. It typically involves an enlargement of breast lobules, which contain more glands than usual. In "sclerosing adenosis," or "fibrosing adenosis," the enlarged lobules are distorted by scar-like fibrous tissue.

"Cysts" are abnormal sacs filled with fluid or semi-solid material. Cysts in the breast are lined by breast epithelial cells, developing from lobular structures. They begin as excess fluid inside breast glands, but may grow to proportions that stretch surrounding breast tissue, causing pain.

"Fibrocysts" are cystic lesions circumscribed by, or situated within, a conspicuous amount of fibrous connective tissue.

"Duct ectasia" refers to a dilation of mammary ducts by lipid and cellular debris. Rupture of the ducts induces infiltration by granulocytes and plasma cells.

"Fibroadenoma" refers to benign tumors that are derived from glandular epithelium and contain a conspicuous stroma of proliferating fibroblasts and connective tissue.

"Fibrosis" simply refers to a prominence of fibrous tissue in the breast.

"Hyperplasia" refers to an overgrowth of cells, where several layers of cells line the basal membrane, without tumor formation. Hyperplasia increases the bulk of mammary tissue. In "epithelial hyperplasia," the cells lining breast ducts and lobules are involved, giving rise to the terms "ductal hyperplasia" and "lobular hyperplasia." Based on a histological determination, hyperplasia may be characterized as "usual" or "atypical".

"Metaplasia" refers to a phenomenon in which a differentiated tissue of one type transforms into a differentiated tissue of another type. Metaplasia often results from an environmental change, and enables cells better to withstand the change.

The compositions of the present invention may be administered in any dosage form and via any system that delivers the active compound endoxifen to breast estrogen receptors in vivo. In some embodiments, a composition of present invention is delivered by "percutaneous administration", e.g., delivering the drug from the surface of patient's skin, through the stratum corneum, epidermis, and dermis layers, and into the microcirculations. This is generally accomplished by diffusion down a concentration gradient. The diffusion may occur via intracellular penetration (through the cells), intercellular penetration (between the cells), transappendageal penetration (through the hair follicles, sweat, and sebaceous glands), or any combination of the above.

Percutaneous administration of the endoxifen composition of the present invention may be advantageous because this may reduce systemic drug exposure and the risks from non-specifically activating estrogen receptors throughout the body. This is because in topical application of endoxifen will absorb primarily into local tissues. When the composition of invention containing endoxifen will be percutaneously applied to breasts, high concentration will accumulate in the breast tissues presumably due to many estrogen receptors therein. The composition of endoxifen may be applied to any skin surface, preferably to one or both breasts. The daily doses to be administered can initially be estimated based upon the absorption coefficients of endoxifen, the breast tissue concentration that is desired, and the plasma concentration that should not be exceeded. The initial dose may be optimized in each patient, depending on individual responses.

Percutaneous administration can be achieved in different ways, such as (i) by mixing the composition of endoxifen with suitable pharmaceutical carriers and, optionally, penetration enhancers to form ointments, emulsions, gel, lotion, creams or the like, where an amount of said preparation is applied onto a certain area of the skin, (ii) by incorporating the composition of endoxifen into patches or transdermal delivery systems according to the technology known in the art.

The effectiveness of percutaneous drug administration depends on many factors, such as drug concentration, surface area of application, time and duration of application, skin temperature, skin hydration, previous irradiation, physicochemical properties of the drug, and partitioning of the drug between the formulation and the skin. In some embodiments, e.g., to enhance percutaneous effectiveness, the compositions or complexes comprise penetration enhancers that improve percutaneous absorption by reducing the resistance of stratum corneum by reversibly altering its physicochemical properties, changing hydration in the stratum corneum, acting as co-solvent, or changing the organization of lipids or proteins in the intracellular spaces. Such enhancers include but are not limited to organic solvents such as alcohol, acetone, dimethylsulfoxide (DMSO), polyethylene glycol, propoylene glycol, fatty acids and fatty alcohol and their derivatives, hydroxyl acids, pyrrolidones, urea, vegetable oils, essential oils, and mixture thereof. In addition to chemical enhancers, physical methods can increase percutaneous absorption. For example, occlusive bandages induce hydration of the skin. Other physical methods include iontophoresis and sonophoresis, which use electrical fields and high-frequency ultrasound, respectively, to enhance absorption of drugs that are poorly absorbed due to their size and ionic characteristics (12-13). Those who are in the pharmaceutical field can easily manipulate the various factors and methods to achieve right efficacious dosage for percutaneous delivery.

For percutaneous administration, the formulation or composition of the invention containing endoxifen may be delivered in the form of ointment, emulsion (lotion), cream, gel, powder, oil or similar formulation. In some embodiments, the formulation comprises excipient additives, including but not limited to vegetable oils such as soybean oil, mustard oil, almond oil, olive oil, groundnut oil, peanut oil, peach kernel oil, groundnut oil, castor oil, canola oil, and the like, animal fats, DMSO, lanolin lipids, phosphatides, hydrocarbons such as paraffin's, petroleum jelly, waxes, lecithin, detergent emulsifying agents, carotin, alcohols, glycerol, glycerol ether, glycerine, glycol, glycol ethers, polyethylene glycol, polypropylene glycol, non-volatile fatty alcohols, acids, esters, volatile alcoholic compounds, talc, urea, cellulose derivatives, coloring agents, antioxidants and preservatives.

In some embodiments the formulation or composition of the invention containing endoxifen may be delivered as transdermal patch. The patch may comprise (i) a solution-impermeable backing foil, (ii) a layer like element having a cavity, (iii) a microporus or semipermeable membrane, (iv) a self-adhesive layer, and (v) optionally a removable backing film. The layer-like element having a cavity may be formed by the backing foil and the membrane. Alternatively, the patch may comprise (i) a solution-impermeable backing foil.(ii) an open-pored foam, a closed pore foam, a tissue like layer or a fibrous web-like layer as reservoir, (iii) a self adhesive layer, and (iv) optionally a removable backing film.

In some preferred embodiments, the composition of the invention containing endoxifen is formulated in hydro alcoholic gel and the amount of endoxifen may vary from 0.001001 to 1.0 gram per 100 grams of gel, most preferably in the range of 0.01-0.20 grams per 100 grams of gel.

In other embodiments, the composition of present invention comprises one or more fatty acid esters as a penetration enhancer. One of the highly preferred examples of a fatty acid ester penetration enhancer is isopropyl myristate. When isopropyl myristate is used in gel, the amount may range e.g., from 0.11 to 5.0 grams per 100 grams of gel, preferably from 0.5 to 2.0 grams per 100 grams of gel.

In another preferred embodiment the composition of invention containing endoxifen may also contain one or more nonaqueous vehicles, such as alcoholic vehicles. Examples of nonaqueous vehicles include ethyl acetate, ethanol, and isopropanol, preferably ethanol and isopropanol. These nonaqueous vehicles may be useful for dissolving both the active agent endoxifen and any other penetration enhancer used. They also preferably have a low boiling point, preferably less than 100° C. at atmospheric pressure, to permit rapid evaporation upon contact with skin. In particular, ethanol may effectively contribute to the percutaneous absorption of endoxifen by rapidly evaporating upon contact with skin. The amount of absolute nonaqueous vehicle in a gel formulation ranges from 35% to 99% by weight, preferably between 50% to 85% and more preferably between 60% to 75%.

In another preferred embodiment, the composition or formulation of the invention comprises an aqueous vehicle that permits solubilization of hydrophilic molecules, and promotes moisturization of skin. An aqueous vehicle also can regulate pH. Aqueous vehicles include alkalinizing and basic buffer solutions, including phosphate buffer solutions, including phosphate buffer solutions (e.g., dibasic or monobasic sodium phosphate); citrate buffered solutions (e.g., sodium citrate or potassium citrate) and purified water. The amount of an aqueous vehicle preferably ranges between 0.10% to 65% by weight of the pharmaceutical composition, preferably between 15% to 50%, and more preferably between 25% to 40%.

In other embodiments, the composition of the invention comprises one or more gelling agents to increase the viscosity of the composition or formulation or to function as a solubilizing agent. It may constitute between 0.1% to 20% by weight of formulation depending on the nature of gelling agent, preferably between 0.5% to 10% and more preferably between 0.5% to 5%. The gelling agents may be carbomers, cellulose derivatives, poloxamers and poloxamines. The preferred gelling agents are chitosan, dextran, pectins, natural gums and cellulose derivatives such as ethyl cellulose, hydroxyethyl cellulose, hydroxypropyl cellulose, hydroxypropyl methyl cellulose (HPMC), carboxymethyl cellulose (CMC) and the like. The most preferred gelling agent is hydroxypropyl cellulose.

The composition of invention may comprise a gelling agent as described above, in particular a non-preneutralized acrylic polymer and also comprise a neutralizing agent. The ratio of neutralizing agent/gelling agent varies in between 10:1 to 0.1:1, preferably between 7:1 to 0.5:1, and more preferably between 4:1 to 1:1. A neutralizing agent in the presence of polymer should form salts that are soluble in the vehicle. A neutralizing agent also should permit optimum swelling of polymer chains during neutralization of charges and formation of polymer salts. The neutralizing agents include ammonium hydroxide, potassium hydroxide, sodium hydroxide, aminomethylpropanol, trolamine, and tromethamine. Those skilled in the art will select a neutralizing agent according to the type of geling agent used in the composition or formulation. However, no neutralizing agent is required when a cellulose derivative will be used as geling agents.

In some embodiments, the compositions of present invention are employed to treat other diseases, and the medication is selected from a lipophilic or a compound made lipophilic by derivatization of the group consisting of antiasthama, antiarrhythmic, antifungals, antihypertensive, anticancer, antibiotics, antidiabetics, antihistamines, antiparasitics, antivirals, cardiac glycosides, hormones, immunotherapies, antihypotensives, steroids, sedatives and analgesics, tranquilizers, vaccines, and cell surface receptor blockers.

The use of terms "a" and "an" and "the" and similar referents in the context of describing the invention (especially in the context of the following claims) are to be construed to cover both the singular and the plural, unless otherwise indicated herein or clearly contradicted by context. The terms "comprising", "including", "having", and "containing" are to be construed as open-ended terms (i.e. meaning "including but not limited to") unless otherwise noted. The use of any and all examples, or exemplary language (e.g., "such as") provided herein, is intended merely to better illuminate the invention and does not pose a limitation on the scope of the invention unless otherwise claimed. No language in the specifications should be constructed as indicating any non-claimed element as essential to the practice of the invention.

Preferred embodiments of this invention are described, including the best mode known to the inventors for carrying out the invention. Variations of those preferred embodiments can become apparent to those of ordinary skilled artisans to employ such variations as appropriate, and the inventors intend for the inventions to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

EXAMPLES

The following examples further illustrate the invention and are not to be construed as in any way as limiting its scope.

Example 1

Synthesis of Compound 3

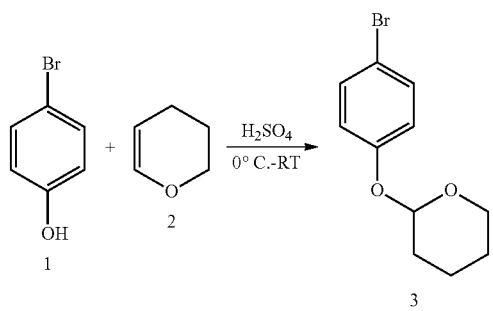

4-Bromophenol (1, 1 kg) and 3, 4-dihydro-2H-pyran (2, 1.5 L) was mixed together in a round bottom flask and cooled to 0° C. Conc. Sulfuric acid (1 mL) was added drop wise while maintaining the temperature below room temperature. The solution was stirred at RT for 1 hr. The reaction solution was diluted with hexane and washed with water (1 L) followed by 5% sodium bicarbonate solution (1 L). The organic layer was dried over sodium sulfate, filtered and evaporated in vacuo at 50-55° C. to give an oil (1.55 Kg). Hexane (300 mL) was added to the oil and triturated to give white solid 3. The suspension was cooled to 0° C. and stirred for 30 min before it was filtered and washed with cold hexane (100 mL) and dried. Yield 1.32 Kg.

Example 2

Synthesis of Compound 5

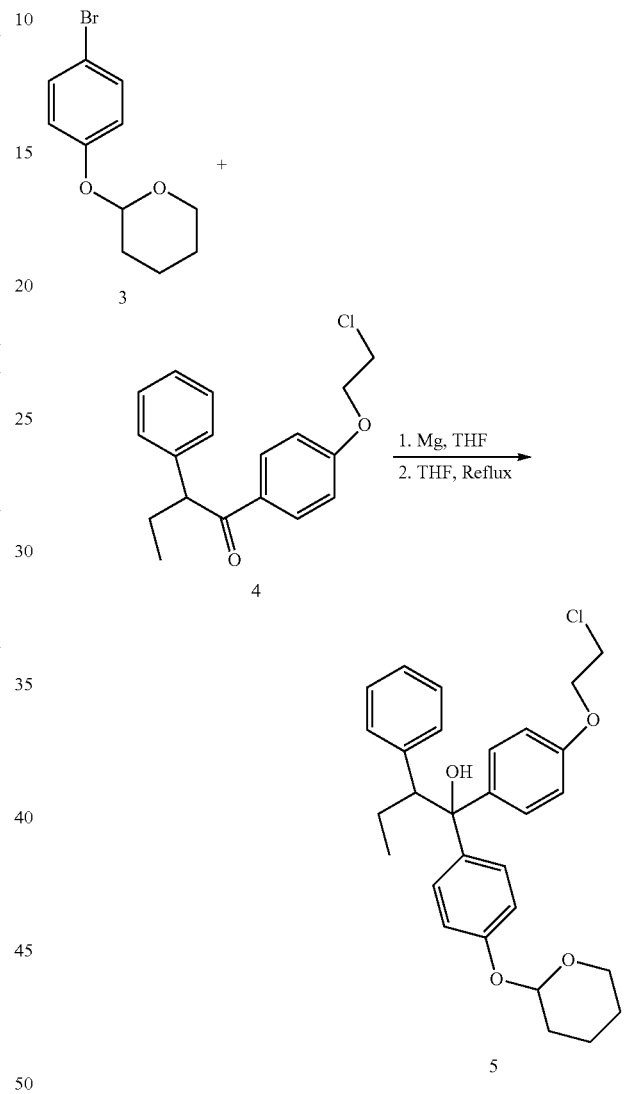

Magnesium turnings (115 g) were added to a 10_L 4-neck round bottom flask containing anhydrous tetrahydrofuran (1 L). The mixture was heated to 55° C. Iodine chips (approx. 5) were added in one lot followed by ethyl bromide (5 mL). Compound 3 (1.1 kg) was dissolved in THF (2 L). 200 mL of this solution was added at once to Mg-THF suspension. The reaction was initiated after 30 mins and reflux started. Remaining solution of compound 3 was added drop wise maintaining the reflux temperature over a period of 1.5 h. The reaction mixture was further refluxed for 2 hr and the cooled to RT. (2-Chloroethoxyphenyl) phenyl butanone (4, 870 g) in THF (1.5 L) was added drop wise over a period of 1 h maintaining the temperature between 30-35° C. The reaction mixture was refluxed for 4 h and cooled to RT. The reaction mixture was poured into ice cold 50% hydrochloric acid (3 L). The organic layer was separated and the aqueous layer was extracted with THF (3×500 mL). The organic layers were combined, dried over sodium sulfate, filtered and concentrated to give 5 as oil which was carried over to next step without further purification. Yield—1.57 kg.

Example 3

Synthesis of Compound 6

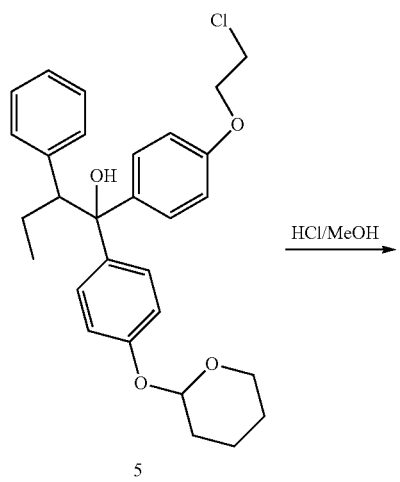

5

Compound (5, 1.57 kg) was dissolved in methanol (6 L) and conc. hydrochloric acid (1.57 kg) was added. The solution was refluxed for 5 h. Methanol was removed in vacuo and dichloromethane (5 L) was added. The organic layer was separated. The aqueous layer was extracted with dichloromethane (2×500 mL). The organic layers were combined and washed with water (2 L), 5% aq. NaHCO$_3$ (2 L), water (2 L), dried over sodium sulfate. Charcoal was added and filtered. The solvent was removed under vacuum to give oil (1.38 kg). The oil was triturated with hexane (5 L) with vigorous stirring to yield 6 as solid product which was filtered and dried. Yield 1.07 kg.

Example 4

Synthesis of Compound I

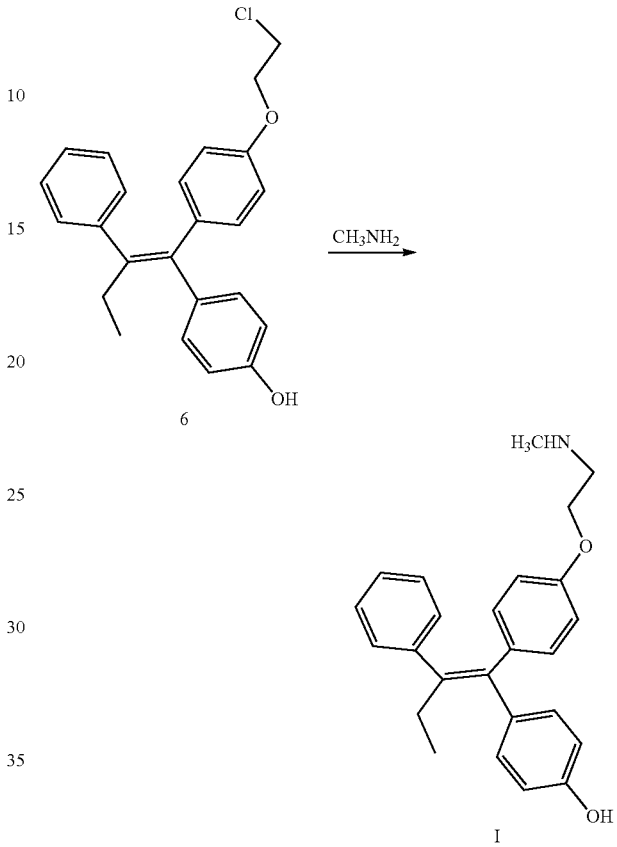

To a solution of compound 6 (50 g) in isopropanol (500 mL), monomethyl amine (300 mL) was added and heated for 24 h maintaining the temperature between 70-75° C. The completion of reaction was monitored by TLC (toluene: triethylamine, 7:3). The solvent was removed in vacuo. Water (500 mL) was added to the residue and extracted with diisopropyl ether (DIPE, 500 mL). The organic layer was separated and the aqueous layer was back extracted with DIPE (200 mL). The organic layers were combined and washed with water (500 mL), 5% aq. sodium bicarbonate (500 mL), dried over sodium sulfate and filtered. The solvent was removed in vacuo to give a gummy residue. Ethyl acetate (50 mL) was added and heated to dissolve the residue completely. The solution was cooled to RT and hexane (50 mL) was added and stirred for 12 h. The solid was filtered and washed with cold ethyl acetate-hexane (1:1, 10 mL) mixture. Product I was dried overnight under high vacuum. Yield 25 g.

Example 5

Endoxifen Solution

Endoxifen solution (1 mg/mL) was prepared by solubilizing endoxifen (10.3 mg) in 0.2% glacial acetic acid (10 mL). The pH (~5.75) of the solution was adjusted with 1N sodium hydroxide (300 μL).

Example 6

Endoxifen Solution

Endoxifen solution (5 mg/mL) was prepared by solubilizing endoxifen (100 mg) in 2% glacial acetic acid (8.6 mL). The solution was diluted with 5% dextrose (10.97 mL). The pH (~5.56) of the solution was adjusted with 5N sodium hydroxide (430 μL).

Example 7

Endoxifen Complexes

A suspension of endoxifen, cholesteryl sulfate, and soy lecithin, is produced by mixing the components together in water and homogenizing using. e.g., a high pressure homogenizer. The resulting suspension can be filtered through 0.2 μm filter and then mixed with 7.5% sucrose solution and lyophilized in either vials or in bulk. The particle size of the resulting complexes is determined using standard procedures, e.g., using a Nicomp particle sizer 380.

Example 8

Endoxifen Complexes

A suspension of endoxifen and soy lecithin is produced by mixing the components together in water and homogenizing using, e.g., a high pressure homogenizer. The resulting suspension can be filtered through 0.2 μm filter and then mixed with 7.5% sucrose solution and lyophilized in either vials or in bulk. The particle size is determined using standard procedures, e.g., using a Nicomp particle sizer 380.

Example 9

Toxicity Testing

Endoxifen was formulated according to Example 6 and was tested for toxicity in male Balb/c mice. A single test dose at 100 mg/kg or 50 mg/kg was intravenously administered to mice. All the mice died at the 100 mg/kg dose level whereas all animals survived at the 50 mg/kg dose level with no significant loss of body weight. The mice also survived in the control group with a vehicle control that lacked endoxifen. Repeat dose toxicity study was conducted with a dose of 25 mg/kg administered consecutively for 3 days with accumulated dose of 75 mg/kg. All the animals in this group survived. The results are reported in the table below as the number of mice surviving per total.

| Treatment | Dose (mg/kg) | Survival/Total |
|---|---|---|
| Single dose | 100 | 0/2 |
|  | 50 | 4/4 |
| Repeat dose | 25 | 4/4 |

Example 10

Endoxifen Exhibits Anti-Proliferative Activity Against Different Tumor Cells Endoxifen was tested for antiproliferation activity against various cancer cell lines from Non Small Lung Cancer, Breast Cancer, Prostate Cancer, Melanoma Cancer, Ovarian Cancer, CNS Cancer, Renal Cancer and Colon Cancers. The cells were incubated for multiple days (3-6) with endoxifen (10 nM to 10 μM) and the inhibition of growth were measured by SRB or MTT staining method. The results indicated significant growth inhibition of cells in the presence of endoxifen ranging from 10 to 100%. Endoxifen induce growth inhibition or cell killing in different tumor cells indicates the usefulness of endoxifen in the treatment of cancers in humans.

Example 11

Endoxifen Inhibits Estradiol Dependent Breast Tumor Growth

It is known that tamoxifen antagonizes estradiol-dependent breast cancer xenograft growth (34). Endoxifen base and endoxifen-citrate in oral dosage form can be similarly be tested for inhibition of estradiol dependent MCF-7 xenograft growth. For the animal experiments, female nude mice (Bom: NMRI-nu/nu) per xenograft experiment, ages 4 to 6 weeks and weighing 20 to 24 g, are used according to standard protocols. An example of such a procedure is as follows:

MCF-7 xenografts are developed by passage of transplantable tumor from a parent tumor established in oophorectomized athymic nude mice treated with estradiol (35).

Randomly bred female athymic mice are bilaterally ovriectomized and allowed a 2-week recovery period before the implantation of tumor material. The s.c. transplantation of the MCF-7 tumor fragments (size, 1×1×1 mm$^3$) is done under anesthesia. The diameter of the tumors is measured regularly, e.g., once weekly, using a caliper-like mechanical instrument and the tumor volume (V) is calculated according to the empirical equation V=(length×width$^2$)/2. The median volumes of each group are normalized to the initial tumor volume resulting in the relative tumor volume. In all the experiments, tumor-bearing mice receive estradiol supplementation [estradiol valerate (E2D), 0.5 mg/kg once/wk i.m.]. This supplementation leads to physiologic levels of serum E2 (25-984 pg/mL) that are comparable to the human situation (25-600 pg/mL depending on the follicular phase).

Substances: The following substances are used: E2D, tamoxifen and endoxifen.

Treatment Modalities: All MCF-7 transplanted animals receive E2D (0.5 mg/kg) injections once a week. After 4 weeks, when hormone-supplemented tumors have grown to ~0.7-0.8 cm in diameter (180-250 mm$^3$), the mice are randomized into 4 treatment groups of 5-10 mice each. The 5-10 mice are sacrificed as baseline controls for E2D alone.

The treatment groups are: (i) E2D support (0.5 mg/kg once/wk i.m); (ii) E2D support (0.5 mg/kg once/wk i.m) plus tamoxifen (0.5 mg-2 mg)/mouse per day, 5 days/week by gavage; (iii) E2D support (0.5 mg/kg once/wk i.m) plus endoxifen (0.5 mg-2 mg)/mouse per day, 5 days/week by gavage; (iv) withdrawal of E2D support.

Suppression of tumor growth in this breast cancer tumor model is indicative of therapeutic effect in the treatment of breast cancer in humans (34).

Example 12

Endoxifen Minimizes Uterotrophic Effect of Estrogen

It is known that tamoxifen is a non-steroidal agent with potent anti-estrogenic effect in animal and in vitro models.

This pharmacologic property is related to the drug's ability to compete with estrogen for estrogen receptors in breast tissues, and to inhibit the stimulatory effect of estrogen on the uterus, vagina and ovaries (36).

Endoxifen (0.1 mg-2 mg) is administered orally once daily for 28 days to determine the reduction in utertrophic effect of estradiol; Female BALB/c mice approximately 50 days old and weighing 19-20 g are obtained (e.g., from Charles-River, Inc.) and housed four to five per cage at a temperature (23+_1 C) and light (12 h light/day). The atrophic changes are observed in the mice. There will be three groups such as vehicle control, tamoxifen and endoxifen. The animals (5-10 mice) are randomly assigned to each group. Daily treatments of intact mice with a dose (e.g., 0.1 mg-2 mg) by gavage of tamoxifen or endoxifen are expected to lead to progressive inhibition of uterine and vaginal weight.

Such results will show that endoxifen has better minimizing uterotrophic effect of estrogen than tamoxifen, and that endoxifen finds use as an effective anti-estrogen. Endoxifen blocking of uterine weight gain stimulated by estrogen can also be demonstrated in immature rats. Endoxifen preparations showing the effects described above find use in the treatment of breast cancer as well as other estrogen-sensitive conditions, such as endometriosis, leiomyomata, and benign breast disease, as well as other estrogen-responsive conditions in men and women.

Example 13

Endoxifen-Caused Decrease of Ki-67 Antigen Expression in Proliferating Breast Cancer Cells Ki-67 is a nuclear non-histone protein. This antigen is absent in quiescent cells and is expressed in proliferating cells and is used as a biomarker (37, 38). Endoxifen base or endoxifen-citrate in oral or injectable form are given to xenograft breast cancer tumor models (e.g., as described above), as well as to breast cancer patients. Immunochemical determination of Ki-67 is done in tumor cells from breast cancer tissues from patients, as well as from mice bearing tumors as described in Example 11. The MIB-1 or similar antibody available from commercial sources such as DAKO, Carpenteria, Calif. is used for immunochemical localization of antigen. Decrease in Ki-67 antigen expression in animals and/or breast cancer patients demonstrate the applicability of endoxifen in treating breast cancers.

Example 14

Endoxifen Reduces IGF-1 Levels in Breast Cancer

It is known for humans that tamoxifen reduces the levels of circulating insulin-like growth factor I (IGF-1). IGF-1 has been used as a surrogate biomarker and predicts the effectiveness of tamoxifen in treatments of breast cancer patients (39). To test the effects of endoxifen preparations of the present invention, endoxifen base or endoxifen-citrate are given orally or injected to experimental animals bearing breast cancer tumors. The concentration of IGF-1 levels in control and xenografted breast tumor is monitored by established assays (e.g., ELISA Kit from Diagnostics Systems Laboratories, London, UK or DAKO, Carpenteria, Calif.). Endoxifen is administered by gavages at 0.5 mg-2 mg per mouse per day, 5 days/week. Decrease of IGF-1 levels and tumor growth reduction indicates the usefulness of IGF-1 as a surrogate marker for breast cancer.

Example 15

Endoxifen Prevents Development of Bicalutamide-Induced Gynecomastia and Breast Pain Bicalutamide (CasodexR) is used for treating prostate cancer in men. There is growing evidence that IGF-1 may be involved in prostate cancer promotion and progression. It is also known that anti-estrogen agents such as tamoxifen decrease IGF-1 levels and prevent biculatamide-induced gynecomastia in prostate cancer patients (40). Since, endoxifen is an active metabolite of the tamoxifen anti-estrogen, the silastic slow-release capsules containing endoxifen for implant or oral doses of endoxifen (1 mg-10 mg/day) with biculatamide are expected to prevent development of biclutamide-induced gynecomastia and breast pain.

Example 16

Inhibition of PKC by Endoxifen In Vitro

Figure 5:
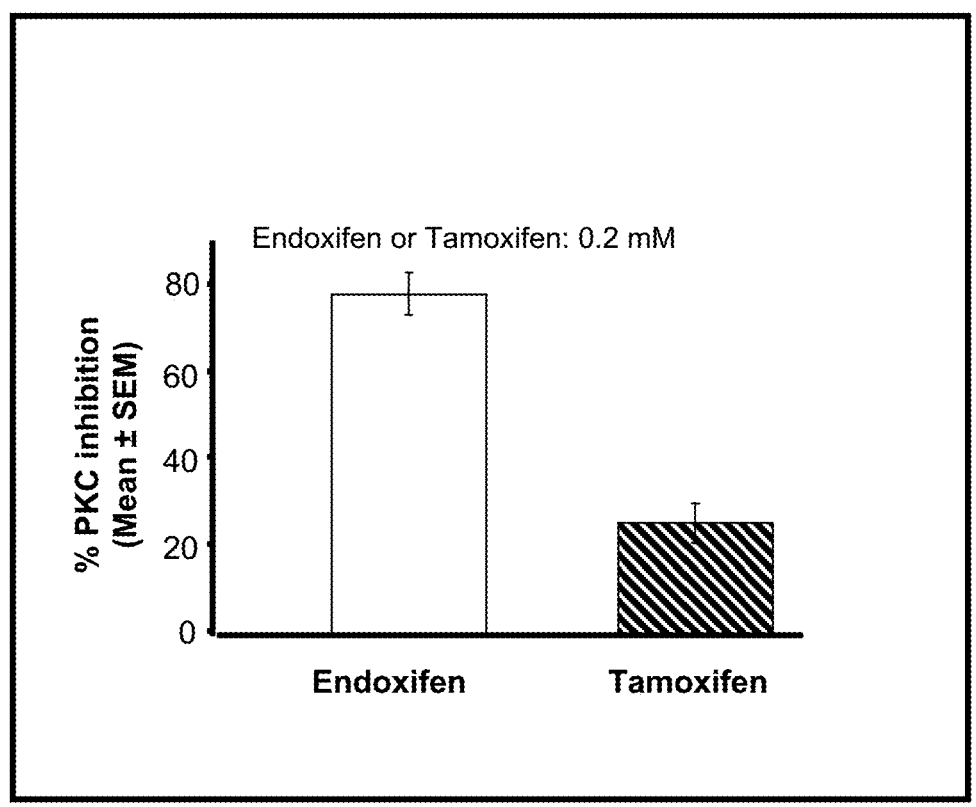
FIG. 5 shows a graph comparing inhibition of PKC activity by endoxifen and tamoxifen.

A PKC kinase activity assay kit (Assay Designs, Ann Arbor, Mich.) was used to test endoxifen PKC inhibitory activity 0.025, 0.05, 0.1, or 0.2 mM endoxifen was used in a reaction mix containing PKC 10 ng/well. Tamoxifen in same concentration was used as a positive control. Endoxifen inhibited PKC activity in concentration dependent manner. The percentage PKC inhibition ranged between 12 and 80 with endoxifen concentration between 0.025 and 0.2 mM, respectively. In comparison, tamoxifen, when tested, was found less potent PKC inhibitor at 0.1 and 0.2 mM resulting 35 and 25% PKC inhibition, respectively; lower concentrations of tamoxifen (0.025 and 0.05 mM) showed negligible PKC inhibition. FIG. 5 shows endoxifen and tamoxifen induced PKC inhibition at 0.2 mM. The study demonstrated that endoxifen is at least four fold more potent PKC inhibitor than tamoxifen, and suggests its role in manic disorder.

Example 17

Endoxifen safety was evaluated in two rodent species. Endoxifen sub-chronic toxicity study was conducted in mice and rats. The results showed that oral administration of endoxifen up to 8 mg/kg in mice or up to 4 mg/kg in rats, daily for 28 days had no mortalities; gross pathological examination did not reveal any abnormality related to the treatment group and animals were free of clinical signs of toxicity.

Example 18

A comparative pharmacokinetic study carried out in rats showed that orally administered endoxifen (10 mg/kg) resulted in 10 fold higher endoxifen plasma concentration as compared to endoxifen concentration after same dose (10 mg/kg) administration of tamoxifen.

All references, including publications, patent applications, and patent cited herein, including those in the list below and otherwise cited in this specification, are hereby incorporated by reference to the same extent as if each reference was individually and specifically indicated to be incorporated by reference and were set forth in the entirely herein.

REFERENCES

1. Furr, B. J., and V. C. Jordan. 1984. The pharmacology and clinical uses of tamoxifen. *Pharmacol Ther* 25:127-205.
2. Osborne, C. K. 1998. Tamoxifen in the treatment of breast cancer. *N Engl J Med* 339:1609-1618.
3. Fisher, B., J. P. Costantino, D. L. Wickerham, C. K. Redmond, M. Kavanah, W. M. Cronin, V. Vogel, A. Robidoux, N. Dimitrov, J. Atkins, M. Daly, S. Wieand, E. Tan-Chiu, L. Ford, and N. Wolmark. 1998. Tamoxifen for prevention of breast cancer: report of the National Surgical Adjuvant Breast and Bowel Project P-1 Study. *J Natl Cancer Inst* 90:1371-1388.
4. Stearns, V., L. Ullmer, J. F. Lopez, Y. Smith, C. Isaacs, and D. Hayes. 2002. Hot flushes. *Lancet* 360:1851-1861.
5. Stearns, V., M. D. Johnson, J. M. Rae, A. Morocho, A. Novielli, P. Bhargava, D. F. Hayes, Z. Desta, and D. A. Flockhart. 2003. Active tamoxifen metabolite plasma concentrations after coadministration of tamoxifen and the selective serotonin reuptake inhibitor paroxetine. *J Natl Cancer Inst* 95:1758-1764.
6. Otton, S. V., S. E. Ball, S. W. Cheung, T. Inaba, R. L. Rudolph, and E. M. Sellers. 1996. Venlafaxine oxidation in vitro is catalysed by CYP2D6. *Br J Clin Pharmacol* 41:149-156.
7. Bijl, M. J., L. E. Visser, A. Hofman, A. G. Vulto, T. van Gelder, B. H. Stricker, and R. H. van Schaik. 2008. Influence of the CYP2D6*4 polymorphism on dose, switching and discontinuation of antidepressants. *Br J Clin Pharmacol* 65:558-564.
8. Manji, H. K., and R. H. Lenox. 2000. The nature of bipolar disorder. *J Clin Psychiatry* 61 Supp 13:42-57.
9. Einat, H., P. Yuan, S. T. Szabo, S. Dogra, and H. K. Manji. 2007. Protein kinase C inhibition by tamoxifen antagonizes manic-like behavior in rats: implications for the development of novel therapeutics for bipolar disorder. *Neuropsychobiology* 55:123-131.
10. Yildiz, A., S. Guleryuz, D. P. Ankerst, D. Ongur, and P. F. Renshaw. 2008. Protein kinase C inhibition in the treatment of mania: a double-blind, placebo-controlled trial of tamoxifen. *Arch Gen Psychiatry* 65:255-263.
11. Zarate, C. A., Jr., J. B. Singh, P. J. Carlson, J. Quiroz, L. Jolkovsky, D. A. Luckenbaugh, and H. K. Manji. 2007. Efficacy of a protein kinase C inhibitor (tamoxifen) in the treatment of acute mania: a pilot study. *Bipolar Disord* 9:561-570.
12. Kulkarni, J., C. Gurvich, H. Gilbert, F. Mehmedbegovic, L. Mu, N. Marston, E. Gavrilidis, and A. de Castella. 2008. Hormone modulation: a novel therapeutic approach for women with severe mental illness. *Aust N Z J Psychiatry* 42:83-88.
13. Dhandapani, K. M., and D. W. Brann. 2002. Protective effects of estrogen and selective estrogen receptor modulators in the brain. *Biol Reprod* 67:1379-1385.
14. O'Neill, K., S. Chen, and R. D. Brinton. 2004. Impact of the selective estrogen receptor modulator, raloxifene, on neuronal survival and outgrowth following toxic insults associated with aging and Alzheimer's disease. *Exp Neurol* 185:63-80.
15. Lim, Y. C., Z. Desta, D. A. Flockhart, and T. C. Skaar. 2005. Endoxifen (4-hydroxy-N-desmethyl-tamoxifen) has anti-estrogenic effects in breast cancer cells with potency similar to 4-hydroxy-tamoxifen. *Cancer Chemother Pharmacol* 55:471-478.
16. Lim, Y. C., L. Li, Z. Desta, Q. Zhao, J. M. Rae, D. A. Flockhart, and T. C. Skaar. 2006. Endoxifen, a secondary metabolite of tamoxifen, and 4-OH-tamoxifen induce similar changes in global gene expression patterns in MCF-7 breast cancer cells. *J Pharmacol Exp Ther* 318: 503-512.
17. DiazGranados, N., and C. A. Zarate, Jr. 2008. A review of the preclinical and clinical evidence for protein kinase C as a target for drug development for bipolar disorder. *Curr Psychiatry Rep* 10:510-519.
18. Kulkarni, J., K. A. Garland, A. Scaffidi, B. Headey, R. Anderson, A. de Castella, P. Fitzgerald, and S. R. Davis. 2006. A pilot study of hormone modulation as a new treatment for mania in women with bipolar affective disorder. *Psychoneuroendocrinology* 31:543-547.
19. Lindamer, L. A., J. B. Lohr, M. J. Harris, and D. V. Jeste. 1997. Gender, estrogen, and schizophrenia. *Psychopharmacol Bull* 33:221-228.
20. Salem, J. E., and A. M. Kring. 1998. The role of gender differences in the reduction of etiologic heterogeneity in schizophrenia. *Clin Psychol Rev* 18:795-819.
21. Hendrick, V., L. L. Altshuler, and V. K. Burt. 1996. Course of psychiatric disorders across the menstrual cycle. *Harv Rev Psychiatry* 4:200-207.
22. Chang, S. S., and D. C. Renshaw. 1986. Psychosis and pregnancy. *Compr Ther* 12:36-41.
23. Steinman, L. 2001. Multiple sclerosis: a two-stage disease. *Nat Immunol* 2:762-764.
24. Whitacre, C. C. 2001. Sex differences in autoimmune disease. *Nat Immunol* 2:777-780.
25. El-Etr, M., S. Vukusic, L. Gignoux, F. Durand-Dubief, I. Achiti, E. E. Baulieu, and C. Confavreux. 2005. Steroid hormones in multiple sclerosis. *J Neurol Sci* 233:49-54.
26. Riggs, B. L., and L. C. Hartmann. 2003. Selective estrogen-receptor modulators—mechanisms of action and application to clinical practice. *N Engl J Med* 348:618-629.
27. Shang, Y., and M. Brown. 2002. Molecular determinants for the tissue specificity of SERMs. *Science* 295:2465-2468.
28. Bebo, B. F., Jr., B. Dehghani, S. Foster, A. Kumiawan, F. J. Lopez, and L. S. Sherman. 2009. Treatment with selective estrogen receptor modulators regulates myelin specific T-cells and suppresses experimental autoimmune encephalomyelitis. *Glia* 57:777-790.
29. Yaffe, K., K. Krueger, S. R. Cummings, T. Blackwell, V. W. Henderson, S. Sarkar, K. Ensrud, and D. Grady. 2005. Effect of raloxifene on prevention of dementia and cognitive impairment in older women: the Multiple Outcomes of Raloxifene Evaluation (MORE) randomized trial. *Am J Psychiatry* 162:683-690.
30. Hornykiewicz, O. 1998. Biochemical aspects of Parkinson's disease. *Neurology* 51:S2-9.
31. Oh, J. D., A. I Geller, G. Zhang, and T. N. Chase. 2003. Gene transfer of constitutively active protein kinase C into striatal neurons accelerates onset of levodopa-induced motor response alterations in parkinsonian rats. *Brain Res* 971:18-30.
32. Smith, C. P., J. D. Oh, F. Bibbiani, M. A. Collins, I. Avila, and T. N. Chase. 2007. Tamoxifen effect on L-DOPA induced response complications in parkinsonian rats and primates. *Neuropharmacology* 52:515-526.
33. O'Neill, K., S. Chen, and R. Diaz Brinton. 2004. Impact of the selective estrogen receptor modulator, tamoxifen, on neuronal outgrowth and survival following toxic insults associated with aging and Alzheimer's disease. Exp Neurol 188:268-278.

34. Johnston, S. R., I. M. Boeddinghaus, S. Riddler, B. P. Haynes, I. R. Hardcastle, M. Rowlands, R. Grimshaw, M. Jarman, and M. Dowsett. 1999. Idoxifene antagonizes estradiol-dependent MCF-7 breast cancer xenograft growth through sustained induction of apoptosis. *Cancer Res* 59:3646-3651.
35. Iino, Y., D. M. Wolf, S. M. Langan-Fahey, D. A. Johnson, M. Ricchio, M. E. Thompson, and V. C. Jordan. 1991. Reversible control of oestradiol-stimulated growth of MCF-7 tumours by tamoxifen in the athymic mouse. *Br J Cancer* 64:1019-1024.
36. Suh, N., A. L. Glasebrook, A. D. Palkowitz, H. U. Bryant, L. L. Burris, J. J. Starling, H. L. Pearce, C. Williams, C. Peer, Y. Wang, and M. B. Sporn. 2001. Arzoxifene, a new selective estrogen receptor modulator for chemoprevention of experimental breast cancer. *Cancer Res* 61:8412-8415.
37. Assersohn, L., J. Salter, T. J. Powles, R. A'Hern, A. Makris, R. K. Gregory, J. Chang, and M. Dowsett. 2003. Studies of the potential utility of Ki67 as a predictive molecular marker of clinical response in primary breast cancer. *Breast Cancer Res Treat* 82:113-123.
38. Kenny, F. S., P. C. Willsher, J. M. Gee, R. Nicholson, S. E. Pinder, I. O. Ellis, and J. F. Robertson. 2001. Change in expression of ER, bcl-2 and MIB1 on primary tamoxifen and relation to response in ER positive breast cancer. *Breast Cancer Res Treat* 65:135-144.
39. Nahta, R., G. N. Hortobagyi, and F. J. Esteva. 2003. Growth factor receptors in breast cancer: potential for therapeutic intervention. *Oncologist* 8:5-17.
40. Saltzstein, D., P. Sieber, T. Morris, and J. Gallo. 2005. Prevention and management of bicalutamide-induced gynecomastia and breast pain: randomized endocrinologic and clinical studies with tamoxifen and anastrozole. *Prostate Cancer Prostatic Dis* 8:75-83.

We claim:

1. A method of inhibiting protein kinase C (PKC) in a subject by delivering endoxifen to the plasma of the subject, the method comprising orally administering to the subject an enteric-coated tablet or enteric-coated capsule containing an amount of a synthetic preparation of endoxifen effective to inhibit PKC in the subject when delivered to the plasma of the subject, wherein:
   i) the synthetic preparation of endoxifen is at least 80% Z-endoxifen; and
   ii) the synthetic preparation of endoxifen is in the form of a citrate salt.

2. The method of claim 1, wherein the subject is a mammal.

3. The method of claim 2, wherein the mammal is human.

* * * * *